(12) United States Patent
Zhang et al.

(10) Patent No.: US 10,160,728 B2
(45) Date of Patent: Dec. 25, 2018

(54) ANTIMICROBIAL IMIDAZOLIUM COMPOUNDS

(71) Applicant: AGENCY FOR SCIENCE, TECHNOLOGY AND RESEARCH, Singapore (SG)

(72) Inventors: Yugen Zhang, Singapore (SG); Siti Nurhanna Binti Riduan, Singapore (SG); Yuan Yuan, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 0 days.

(21) Appl. No.: 15/511,631

(22) PCT Filed: Sep. 15, 2015

(86) PCT No.: PCT/SG2015/050318
§ 371 (c)(1),
(2) Date: Mar. 15, 2017

(87) PCT Pub. No.: WO2016/043660
PCT Pub. Date: Mar. 24, 2016

(65) Prior Publication Data
US 2017/0291877 A1  Oct. 12, 2017

(30) Foreign Application Priority Data
Sep. 15, 2014  (SG) ............ 10201405746V

(51) Int. Cl.
| | |
|---|---|
| *C07D 233/56* | (2006.01) |
| *A01N 43/50* | (2006.01) |
| *A61K 9/00* | (2006.01) |
| *A61K 47/10* | (2017.01) |
| *A61K 9/06* | (2006.01) |
| *A01N 25/04* | (2006.01) |
| *A61K 8/04* | (2006.01) |
| *A61K 8/49* | (2006.01) |
| *A61Q 17/00* | (2006.01) |

(52) U.S. Cl.
CPC .......... *C07D 233/56* (2013.01); *A01N 25/04* (2013.01); *A01N 43/50* (2013.01); *A61K 8/042* (2013.01); *A61K 8/4946* (2013.01); *A61K 9/0014* (2013.01); *A61K 9/06* (2013.01); *A61K 47/10* (2013.01); *A61Q 17/005* (2013.01)

(58) Field of Classification Search
CPC ............................................ C07D 233/56
See application file for complete search history.

(56) References Cited

U.S. PATENT DOCUMENTS

| | | | | |
|---|---|---|---|---|
| 3,853,907 A | * | 12/1974 | Edwards | .................. 548/313.7 |
| 3,911,133 A | * | 10/1975 | Edwards | ............. A61K 8/4946 |
| | | | | 424/54 |
| 6,416,770 B1 | | 7/2002 | Leduc et al. | |

FOREIGN PATENT DOCUMENTS

| | | |
|---|---|---|
| WO | WO 2012/050531 A1 | 4/2012 |
| WO | WO 2014/025314 A1 | 2/2014 |

OTHER PUBLICATIONS

Baker, Journal of Organometallic Chemistry, vol. 691, p. 5845-5855. (Year: 2006).*
Siti Nurhanna Riduan, et al., Imidazolium salts and their polymeric materials for biological applications, Chem. Soc. Rev., vol. 42(23), pp. 9055-9070 (Dec. 7, 2013).
PCT International Search Report, 4 pgs., (dated Oct. 29, 2015).
PCT Written Opinion of the International Searching Authority, 7 pgs., (dated Oct. 29, 2015).
PCT Notification concerning Transmittal of International Preliminary Report on Patentability (Chapter 1 of the Patent Cooperation Treaty), 8 pgs., (dated Mar. 21, 2017).
Lihong Liu, et al., "Self-assembled cationic peptide nanoparticles as an efficient antimicrobial agent," Nature Nanotechnology, vol. 4, pp. 457-463 (Jul. 2009).
J.W. Costerton, et al., "Bacterial communications in implant infections: A target for an intelligence war," The International Journal of Artificial Organs, vol. 30, Iss. 9, pp. 757-763 (Sep. 2007).
Y.H. An, et al., "Effects of sterilization on implant mechanical property and biocompatibility," The International Journal of Artificial Organs, vol. 28, Iss. 11, pp. 1126-1137 (Nov. 2005).
M. Zasloff, "Antimicrobial peptides of multicellular organisms," Nature, vol. 415, pp. 389-395 (Jan. 24, 2002).
S. Fernandez-Lopez, et al., "Antibacterial agents based on the cyclic D,L-alpha-peptide architecture," Nature, vol. 412, pp. 452-455 (Jul. 26, 2001).
A.K. Marr, et al., "Antibacterial peptides for therapeutic use: obstacles and realistic outlook," Curr. Opin. Pharmacol., vol. 6, Iss. 5, pp. 468-472 (Aug. 4, 2006).
E. -R. Kenawy, et al., "The Chemistry and Applications of Antimicrobial Polymers: A State-of-the-Art Review," Biomacromolecules, vol. 8, No. 5, pp. 1359-1384 (May 2007).
Z. Oren, et al., "Cyclization of a Cytolytic Amphipathic α-Helical Peptide and Its Diastereomer: Effect on Structure, Interaction with Model Membranes, and Biological Function," Biochemistry, vol. 39, Iss. 20, pp. 6103-6114 (Apr. 29, 2000).

(Continued)

*Primary Examiner* — Rebecca L Anderson
*Assistant Examiner* — Karen Cheng
(74) *Attorney, Agent, or Firm* — Womble Bond Dickinson (US) LLP

(57) ABSTRACT

The present invention relates to antimicrobial imidazolium compounds having the structure of Formula (I) wherein R is an optionally substituted aliphatic group that is linear, cyclic, saturated, unsaturated or any combination thereof; n is an integer of at least 1; and X is an anionic counterion. The present invention also relates to pharmaceutical composition comprising the compound, a gel comprising the compound, uses of the compound as an antibiotic and methods for the preparation of the gels.

10 Claims, 8 Drawing Sheets

(56) References Cited

OTHER PUBLICATIONS

E.F. Palermo, et al., "Chemical Structure of Cationic Groups in Amphiphilic Polymethacrylates Modulates the Antimicrobial and Hemolytic Activities," Biomacromolecules, vol. 10, No. 6, pp. 1416-1428 (2009).
N. Pasquier, et al., "From Multifunctionalized Poly(ethylene imine)s toward Antimicrobial Coatings," Biomacromolecules, vol. 8, Iss. 9, pp. 2874-2882 (2007).
Y. Zhang, et al., "Colloidal poly-imidazolium salts and derivatives," Nano Today, vol. 4, Iss. 1, pp. 13- 20 (Feb. 2009).
C. Zhou, et al., "A photopolymerized antimicrobial hydrogel coating derived from epsilon-poly-L-lysine," Biomaterials, vol. 32, Iss. 11, pp. 2704-2712 (Apr. 2011).
Y. Qiao, et al., "Highly dynamic biodegradable micelles capable of lysing Gram-positive and Gram-negative bacterial membrane," Biomaterials, vol. 33, Iss. 4, pp. 1146-1153 (Feb. 2012).
A. C. Engler, et al., "Emerging trends in macromolecular antimicrobials to fight multi-drug-resistant infections," NanoToday, vol. 7, Iss. 3, pp. 201-222 (Jun. 2012).
L. Liu, et al., "Main-chain imidazolium oligomer material as a selective biomimetic antimicrobial agent," Biomaterials, vol. 33, Iss. 33, pp. 8625-8631 (Nov. 2012).
L. Liu, et al., "Short imidazolium chains effectively clear fungal biofilm in keratitis treatment," Biomaterials, vol. 34, Iss. 4, pp. 1018-1023 (Jan. 2013).
Francesca D'Anna, et al., "Geminal Imidazolium Salts: A New Class of Gelators," Langmuir, vol. 28, No. 29, pp. 10849-10859 (Jul. 24, 2012).
W. Chin, et al., "Biodegradable Broad-Spectrum Antimicrobial Polycarbonates: Investigating the Role of Chemical Structure on Activity and Selectivity," Macromolecules, vol. 46, Iss. 22, pp. 8797-8807 (2013).
Daphne A. Salick, et al, "Inherent Antibacterial Activity of a Peptide-Based β-Hairpin Hydrogel," J. Am. Chem. Soc., vol. 129, Iss. 47, pp. 14793-14799 (Nov. 28, 2007).
P. Li, et al., "A polycationic antimicrobial and biocompatible hydrogel with microbe membrane suctioning ability," Nat. Mater., vol. 10, pp. 149-156 (Feb. 2011).
M.F. Ilker, et al., "Tuning the Hemolytic and Antibacterial Activities of Amphiphilic Polynorbornene Derivatives,"J. Am. Chem. Soc., vol. 126, pp. 15870-15875 (2004).
G.N. Tew, et al., "De Novo Design of Antimicrobial Polymers, Foldamers, and Small Molecules: From Discovery to Practical Applications,"Acc. Chem. Res., vol. 43, No. 1, pp. 30-39 (Jan. 19, 2010).
B. Gao, et al., "Studies on the preparation and antibacterial properties of quaternized polyethyleneimine," J. Biomater. Sci., Polym. Ed., vol. 18, Iss. 5, pp. 531-544 (2007).
Y. Li, et al., "Broad-Spectrum Antimicrobial and Biofilm-Disrupting Hydrogels: Stereocomplex-Driven Supramolecular Assemblies" Angew. Chem. Int. Ed., vol. 52, Iss. 5, pp. 674-676 (Jan. 7, 2013).
Carla Rizzo, et al., "Two-Component Hydrogels Formed by Cyclodextrins and Dicationic Imidazolium Salts," Eur. J. Org. Chem., vol. 2014, Iss. 5, pp. 1013-1024 (Feb. 2014).
F.J. Leinweber, "Possible Physiological Roles of Carboxylic Ester Hydrolases," Drug Metab. Res., vol. 18, Iss. 4, pp. 379-439 (1987).
G. Bell and PH Gouyon, "Arming the enemy: the evolution of resistance to self-proteins," Microbiology, vol. 149, pp. 1367-1375 (2003).
Remington's Pharmaceutical Sciences, 18[th]Edition, Mack Publishing Co., Easton, PA, pp. xv, xvi, 1444, and 1445 (1990).
Extended European Search Report for counterpart EP Application No. 15842126.3, 9 pgs. (Feb. 16, 2018).
A. Tulloch, et al., "N-Functionalised heterocyclic carbine complexes of silver," XP002777876, J. Chem. Soc. Dalton Trans., vol. 24, pp. 4499-4506 (Dec. 1, 2000).
John R. Miecznikowski, et al., "Transfer hydrogenation reduction of ketones, aldehydes and imines using chelated iridium (III) N-heterocyclic bis-carbene complexes," XP004627350, Polyhedron, vol. 23, No. 17, pp. 2857-2872 (Nov. 11, 2004).
Siti Nurhanna Riduan, et al., "Imidazolium salts and their polymeric materials for biological applications," XP055419248, Chem Soc Rev, vol. 42, No. 23, pp. 9055-9070 (2013).
Yugen Zhang, et al., "Colloidal poly-imidazolium salts and derivatives," Nano Today, vol. 4, Iss. 1, pp. 13-20 (Feb. 2009).
Lihong Liu, et al., "Main-chain imidazolium oligomer material as a selective biomimetic antimicrobial agent," Biomaterials, vol. 33, Iss. 33, pp. 8625-8631 (Nov. 2012).
Lihong Liu, et al., "Short imidazolium chains effectively clear fungal biofilm in keratitis treatment," Biomaterials, vol. 34, Iss. 4, pp. 1018-1023 (Jan. 2013).
Franz-Josef Leinweber, "Possible Physiological Roles of Carboxylic Ester Hydrolases," Drug Metabolism Reviews, vol. 18, Iss. 4, pp. 379-439 (1987).
Cesar A. Arias, et al., "Antibiotic-Resistant Bugs in the 21st Century—A Clinical Super-Challenge," N. Engl. J. Med., vol. 360, pp. 439-443 (Jan. 29, 2009).
Guangshun Wang, et al., "APD2: the updated antimicrobial peptide database and its application in peptide design," Nucleic Acids Research, vol. 37, pp. D933-D937 (2009).
Hancock, R. E. W. & Sahl, H. G., "Antimicrobial and host-defense peptides as new anti-infective therapeutic strategies," Nature Biotechnol., vol. 24, No. 12, pp. 1551-1557 (Dec. 2006).
A.K. Marr, et al., "Antibacterial peptides for therapeutic use: obstacles and realistic outlook," Curr. Opin. Pharmacol., vol. 6, Iss. 5, pp. 468-472 (Oct. 2006).
K. A. Brogden, "Antimicrobial peptides: pore formers or metabolic inhibitors in bacteria?," Nat Rev Microbiol, vol. 3, pp. 238-250 (Mar. 2005).
J.G. Hurdle, et al., "Targeting bacterial membrane function an underexploited mechanism for treating persistent infections," Nat. Rev. Microbiol., vol. 9, No. 1, pp. 62-75 (Jan. 2011).
Dr. Kieron M. G. O'Connell, "Combating Multidrug-Resistant Bacteria: Current Strategies for the Discovery of Novel Antibacterials," Angew. Chem. Int. Ed., vol. 52, Iss. 41, pp. 10706-10733 (Oct. 4, 2013).
A. Munoz-Bonilla, et al., "Polymeric materials with antimicrobial activity," Prog. Polym. Sci., vol. 37, lss. 2, pp. 281-339 (Feb. 2012).
K. Kuroda, et al., "The Role of Hydrophobicity in the Antimicrobial and Hemolytic Activities of Polymethacrylate Derivatives," Chem. Eur. J., vol. 15, No. 5, pp. 1123-1133 (2009).
K. Lienkamp, et al., "Antimicrobial Polymers Prepared by ROMP with Unprecedented Selectivity: A Molecular Construction Kit Approach," J. Am. Chem. Soc., vol. 130, No. 30, pp. 9836-9843 (Jul. 30, 2008).
K. Lienkamp, et al., ""Doubly Selective" Antimicrobial Polymers: How Do They Differentiate between Bacteria?," Chem. Eur. J., vol. 15, Iss. 43, pp. 11710-11714 (Nov. 2, 2009).
Fredrik Nederberg, et al., "Biodegradable nanostructures with selective lysis of microbial membranes," Nat. Chem., vol. 3, pp. 409-414 (May 2011).

* cited by examiner

[Fig. 1]
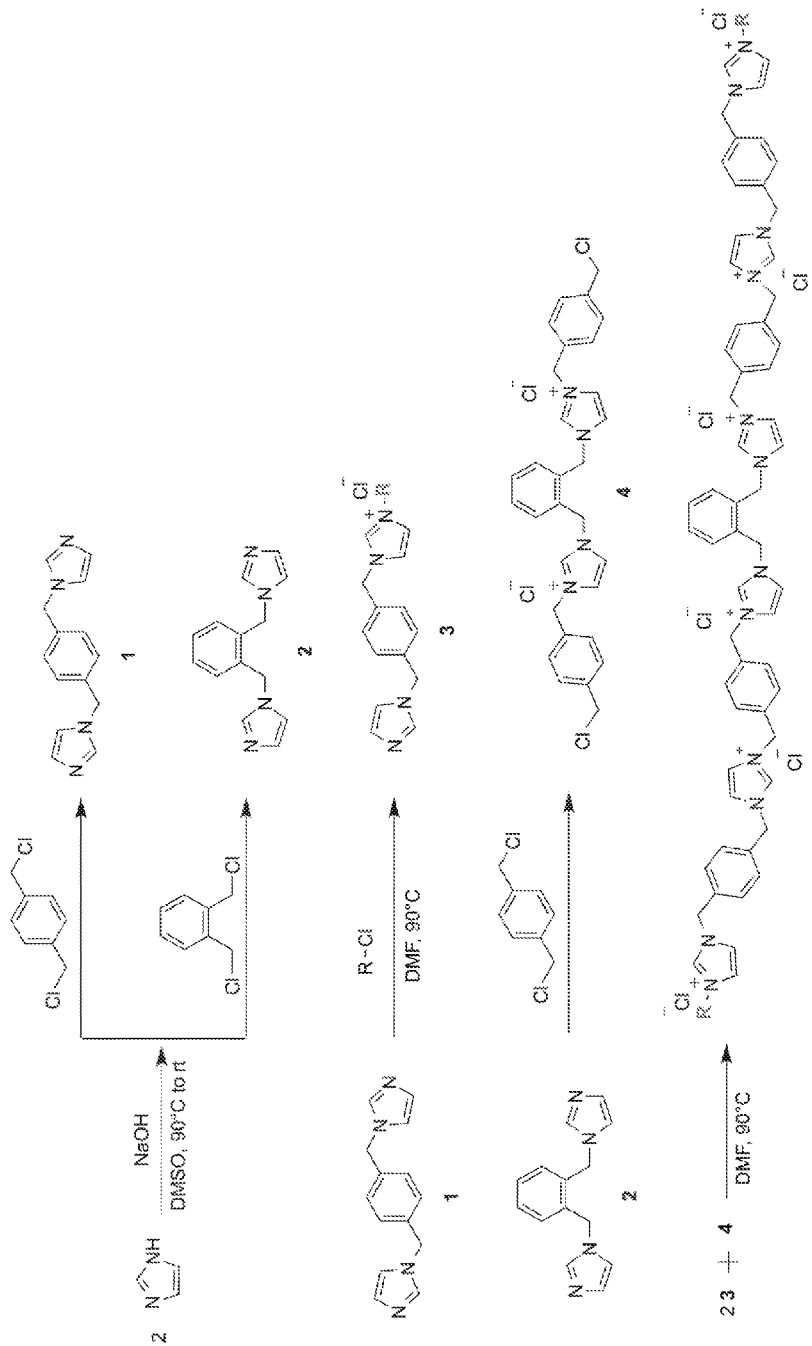

[Fig. 2]
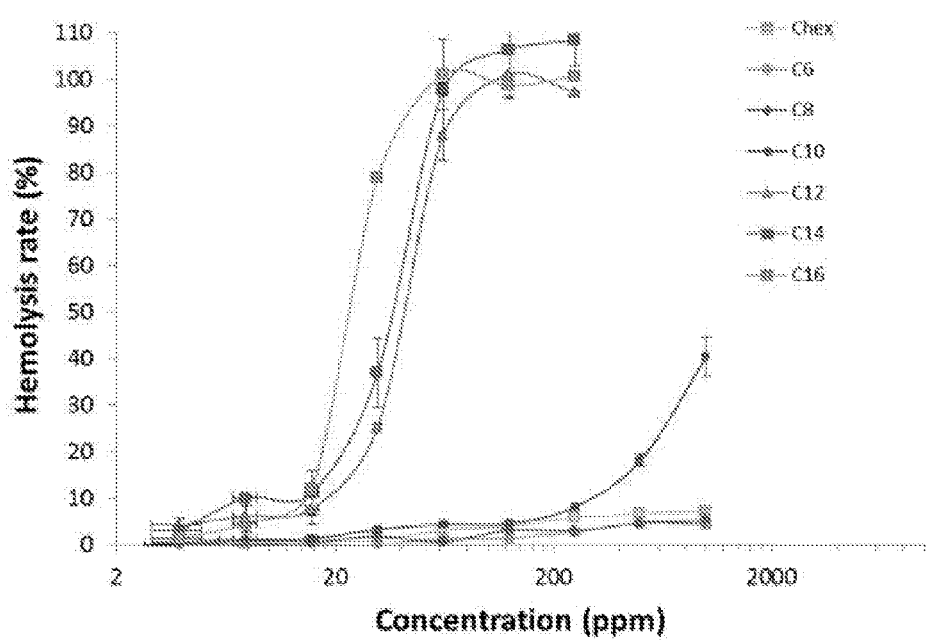

[Fig, 3]
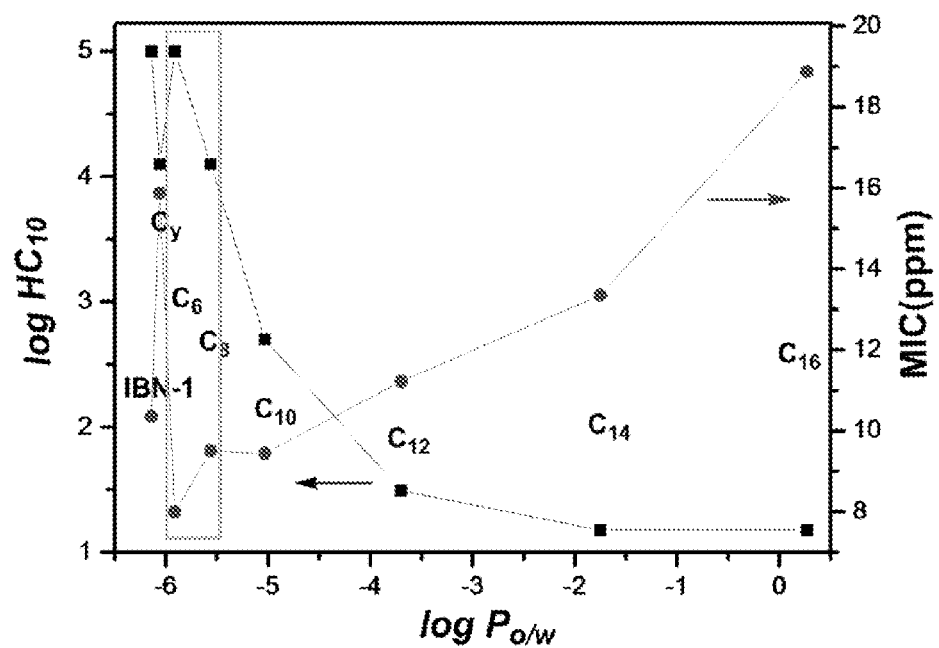

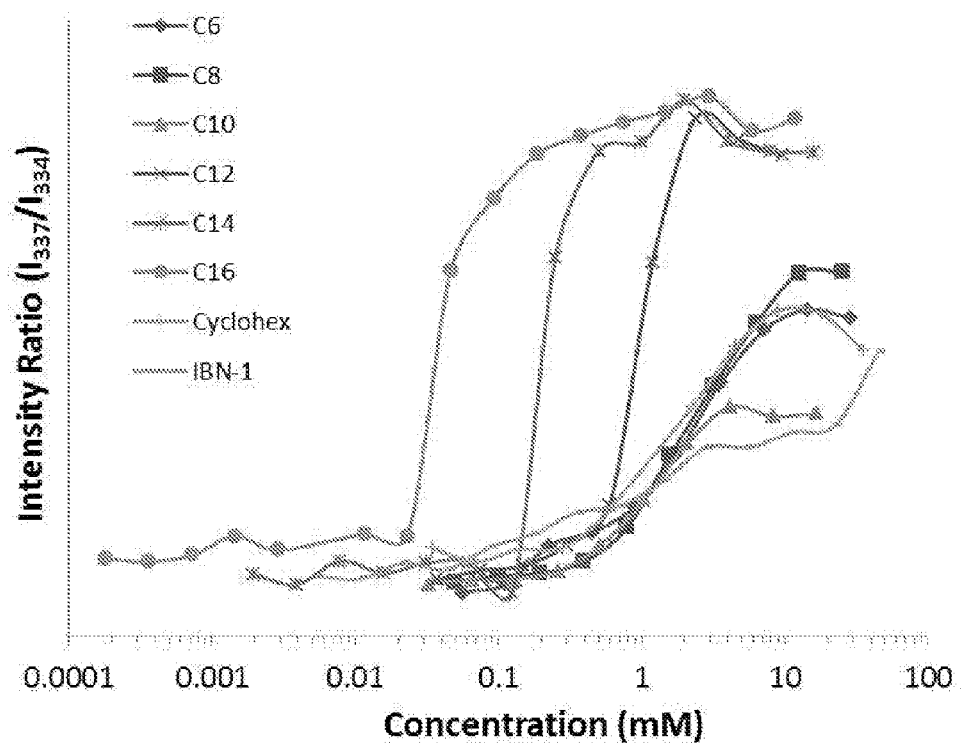
[Fig. 4]

[Fig. 5]
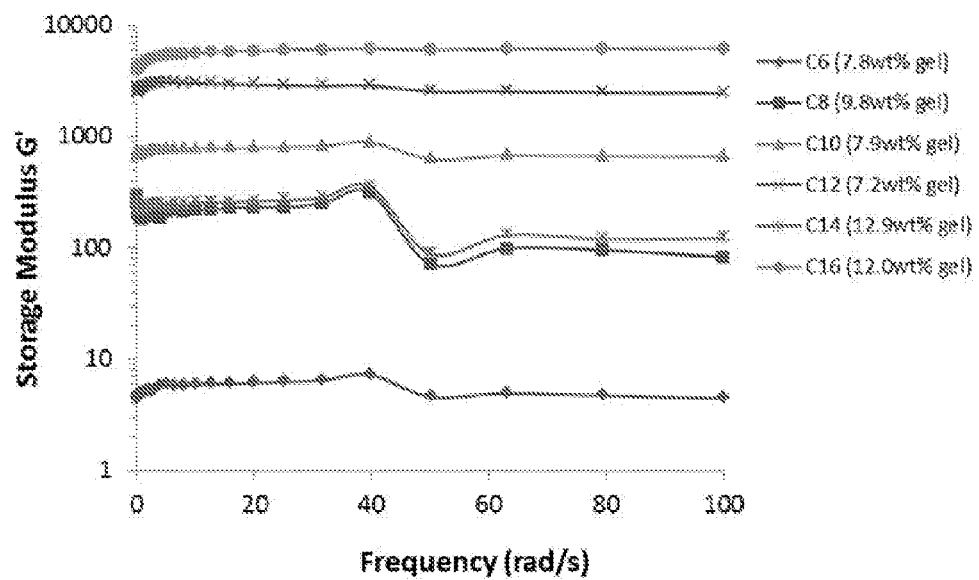

[Fig. 6]
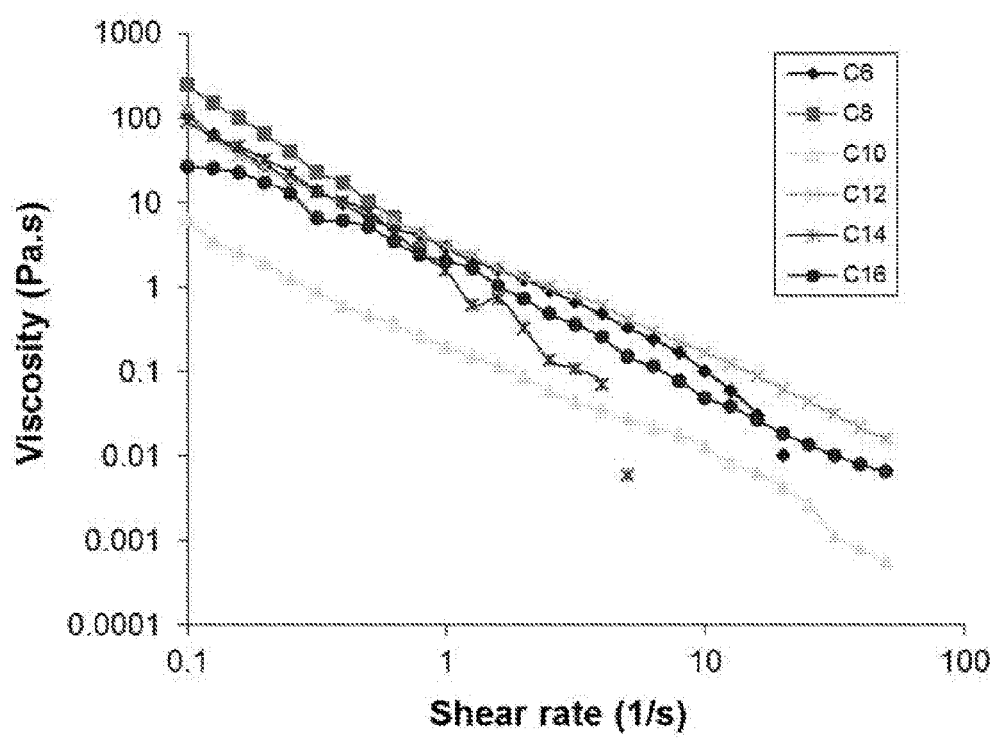

[Fig. 7]
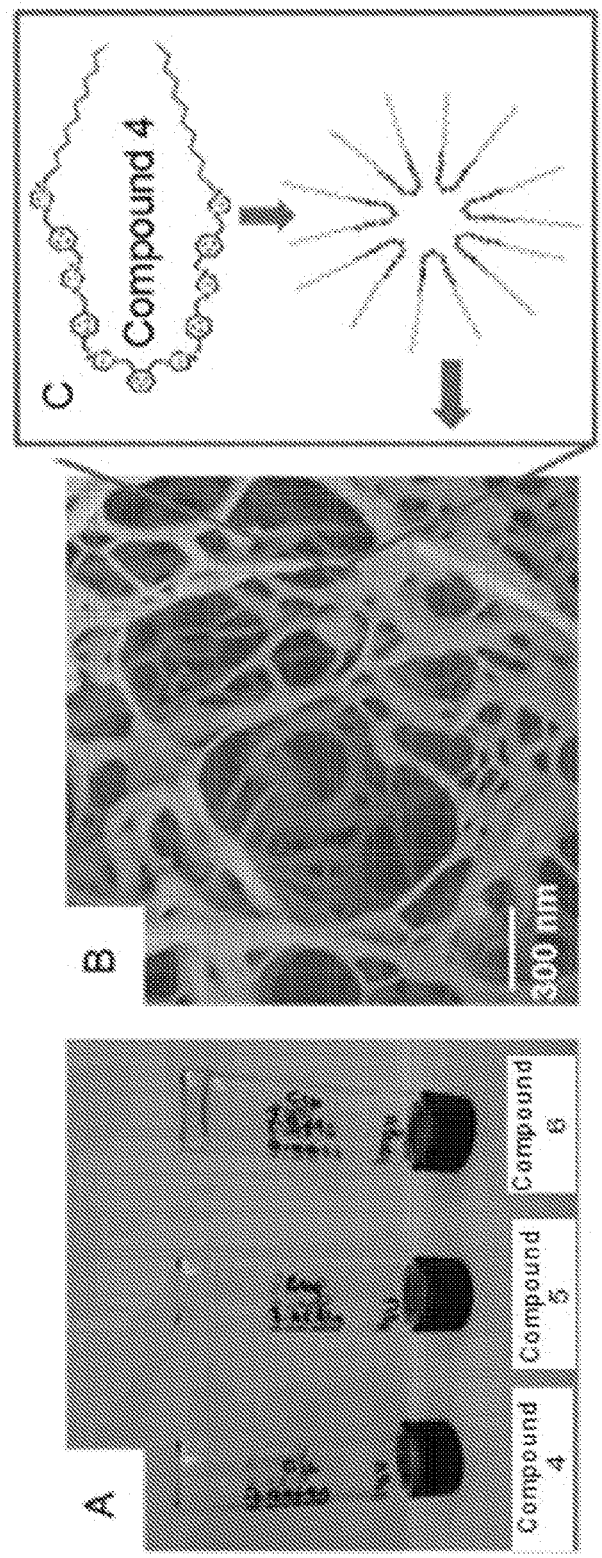

[Fig. 8]
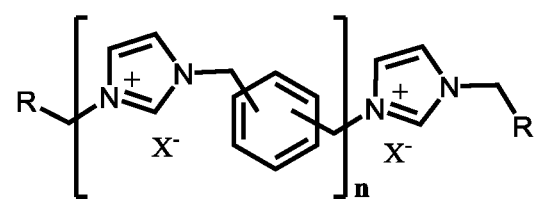
Formula (I)

ANTIMICROBIAL IMIDAZOLIUM COMPOUNDS

CROSS-REFERENCE TO RELATED APPLICATIONS

This patent application is a National Phase Application under 35 U.S.C. § 371 of International Application No, PCT/SG2015/050318, flied Sep. 15, 2015, entitled ANTIMICROBIAL IMIDAZOLIUM COMPOUNDS, which claims priority from Singapore Application No. 10201405746V, filed Sep. 15, 2014.

TECHNICAL FIELD

The present invention generally relates to antimicrobial imidazolium oligomer compounds, pharmaceutical composition comprising the compound, a gel comprising the compound, uses of the compound as an antibiotic and methods for the preparation of the gels.

BACKGROUND ART

Infectious diseases and the increasing threat of worldwide pandemics have underscored the importance of antibiotics and hygiene. Microbial infection is of a grave concern for various commercial applications such as medical devices, hospital surfaces, textiles, food packaging, children's toys, electrical appliances, as well as dental equipment. In the US, hospital-acquired infections affect 2 million people annually, resulting in 90,000 deaths. Additionally, biomaterial-centered infections are common, accounting for 45% of all nosocomial infections, even with prior sterilization and implementation of high levels of disinfection. Common hygiene or sterilization procedures do help to limit the infection; however, the results rely highly on the strength of biocides or techniques. The harsh sterilization techniques commonly used such as irradiation or ethylene oxide/bleach treatment may alter the property of the material essential for the device's performance and are not suitable for most of the applications. The development of a new sterilization method that is mild while ultra-efficient and can selectively kill broad spectrum of micro-organisms instantly is thus of high demand.

Antimicrobial peptides (AMP) have attracted tremendous attention as an alternative to traditional antibiotics. AMPs exhibit a selective membrane-disruptive activity, demonstrating a fast killing mechanism and the potential to deal with drug-resistance issues usually associated with conventional antibiotics. However, the high cost of manufacture and poor half-lives of AMPs in vivo has also limited its applications in healthcare and hygiene.

In addition, while most antimicrobial materials can assume amphiphilic structures, self-gelation of such amphiphilic structures is often not realized. There have been reports of antimicrobial materials that can assemble to hydrogels including peptides and block polymers based on chitin and lactic acid materials. However, these assembly processes are typically triggered by co-gelation polymers or by grafting the antimicrobial material with other polymers.

There is therefore a need to provide a compound that overcomes, or at least ameliorates, one or more of the disadvantages of the effects as described above. There is also a need to provide a pharmaceutical composition comprising the compound, a gel comprising the compound, the use of the compound, pharmaceutical composition or gel as an antibiotic or to kill or inhibit the growth of a microorganism, and a method for synthesizing the gel

SUMMARY

In a first aspect, there is provided a compound having the following formula (I):

[CHEM. 1]

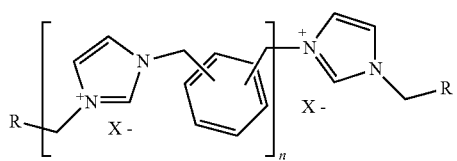

Formula (I)

wherein R is an optionally substituted aliphatic group that is linear, cyclic, saturated, unsaturated or any combination thereof; n is an integer of at least 1; and X is an anionic counterion.

In an embodiment, the compound may have the following Formula (II):

[CHEM. 2]

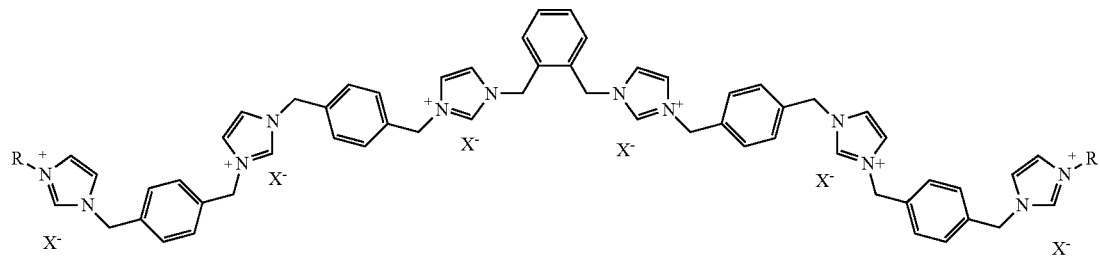

Formula (II)

wherein R may be selected from the group consisting of cyclohexylmethyl ($C_6H_{11}CH_2$), hexyl ($C_6H_{13}$), octyl ($C_8H_{17}$), decyl ($C_{10}H_{21}$), dodecyl ($C_{12}H_{25}$), tetradecyl ($C_{14}H_{29}$), hexadecyl ($C_{16}H_{33}$) and any mixture thereof.

In an embodiment, the compound may be amphiphilic. The amphiphilicity may be due to the presence of both a hydrophilic group (quaternary ammonium salts) and lipophilic group (amphiphilic group). Advantageously, the compound as described above may be amphiphilic because the hydrophilic groups are in the centre of the molecule, which are flanked by hydrophobic groups on the outer side of the molecule.

Advantageously, the compound may be an antimicrobial peptide (AMP)-mimicking imidazolium main-chain polymer that has antibiotic characteristics. AMP mimic imidazolium main-chain polymers may be applied as antimicrobials and in anti-fungal treatments. Advantageously, the imidazolium compounds may possess broad spectrum antimicrobial properties, against a wide range of gram-positive, gram-negative and fungal microorganisms. More advantageously, the AMP-mimicking imidazolium polymer may exhibit selective membrane-disruptive activity, demonstrating a fast killing mechanism of microorganisms and the potential to deal with drug resistance issues usually associated with conventional antibiotics. By tuning the R substituents and hence the amphiphilic structure, the novel imidazolium compounds may demonstrate ultra-efficient antimicrobial activity over a broad-spectrum of microorganisms, where instant and selective bacterial kill (99.999% killing at the minimum inhibitory concentration (MIC)) is achieved, while preventing hemolysis, even at higher concentrations. Advantageously, he long n-alkyl chains at the R positions may facilitate the self-assembly processes, and may therefore enhance antimicrobial activity.

More advantageously, the compound as defined above may be a polymer that may have similar structural characteristics to that of AMPs. The compound may have a fine balance of charge, due to attachment of quaternary ammonium salts, and hydrophobicity, due to the presence of long alkyl chains. With the well-balanced amphiphilic structure, the compound may also be able to self-assemble to form gels in alcohols. This may in turn ascertain their efficacy and selectivity as an antimicrobial agent. The interesting properties of these novel imidazolium compounds suggest a great potential for its utility in common hygiene, sterilization and other health care applications.

Further advantageously, the compound as defined above may have vast structural diversity that may be obtained by multi-step organic synthesis for ease of tuning the final amphiphilicity of the polymer. This may in turn dictate the selectivity and efficacy of the compound as an antibiotic.

In a second aspect, there is provided a pharmaceutical composition comprising a compound of statement 1, or a pharmaceutically acceptable salt or hydrate thereof, in association with a pharmaceutically acceptable carrier.

Advantageously, the compound as defined above has superior antibiotic activity while no effect on higher organisms. It may therefore be suitable for use in vivo.

In a third aspect, there is provided a gel comprising the compound as defined above and a solvent.

Advantageously, the compound as defined above may be able to self-assemble to form gels in alcohols due to the well-balanced amphiphilic structure. More advantageously, the gels may be stable at ambient temperatures, and may be thixotropic. The gels may be weak gels that may be fluid matrix organogels in which the only forces holding them together are simple chain entanglements. As most existing amphiphilic antimicrobial materials can only form by triggering with a co-gelation polymer or grafting antimicrobial material with other copolymers, the compound as defined above has the advantageous property that it may self-assemble to form a gel. The unique sandwich-type amphiphilic structure of the imidazolium oligomer compounds disclosed herein provides novel properties including highly active antimicrobial activities and the added ability to self-assemble to organogels.

In a fourth aspect, there is provided a use of the compound as defined above, the pharmaceutical composition as defined above or the gel as defined above, as an antibiotic.

In a fifth aspect, there is provided a use of the compound as defined above, the pharmaceutical composition as defined above or the gel as defined above, to kill or inhibit the growth of a microorganism.

In an embodiment, the microorganism may be is a bacterium, archaea, fungus, protist, animal, plant, or any mixture thereof.

Advantageously, the compound as defined above, the pharmaceutical composition as defined above or the gel as defined above may be used as an antibiotic or to kill or inhibit the growth of a microorganism. The compound, its pharmaceutical composition or its gel may have ultra-efficient antimicrobial activity over a broad-spectrum of microorganisms, where instant and selective bacterial kill (99.999% killing at the minimum inhibitory concentration (MIC)) may be achieved, while preventing hemolysis, even at higher concentrations. More advantageously, this may result in the use of the compound, pharmaceutical composition or gel in applications for sterilization, including antimicrobial handrubs and surface treatments.

In a sixth aspect, there is provided a method for synthesizing the gel as defined above, comprising the steps of:
  providing the compound as defined above;
  adding a solvent; and
  mixing the compound and the solvent;
  provided that an additional gelation-initiator is not added to the mixture.

In a seventh aspect, there is provided a method for synthesizing the gel as defined above, consisting the steps of:
  providing the compound as defined above;
  adding a solvent; and
  mixing the compound and the solvent.

Advantageously, the method for synthesizing the gel may not require the addition of co-gelation polymer or grafting of copolymers to initiate the gelling process.

Definitions

In this specification a number of terms are used which are well known to a skilled addressee. Nevertheless for the purposes of clarity a number of terms will be defined. The following words and terms used herein shall have the meaning indicated:

In the definitions of a number of substituents below it is stated that "the group may be a terminal group or a bridging group". This is intended to signify that the use of the term is intended to encompass the situation where the group is a linker between two other portions of the molecule as well as where it is a terminal moiety. Using the term alkyl as an example, some publications would use the term "alkylene" for a bridging group and hence in these other publications there is a distinction between the terms "alkyl" (terminal group) and "alkylene" (bridging group). In the present application no such distinction is made and most groups may be either a bridging group or a terminal group.

"Alkenyl" as a group or part of a group denotes an aliphatic hydrocarbon group containing at least one carbon-carbon double bond and which may be straight, linear or branched preferably having 2-12 carbon atoms, more preferably 2-10 carbon atoms, most preferably 2-6 carbon atoms, in the normal chain. The group may contain a plurality of double bonds in the normal chain and the orientation about each is independently E or Z. Exemplary alkenyl groups include, but are not limited to, ethenyl, propenyl, butenyl, pentenyl, hexenyl, heptenyl, octenyl and nonenyl. The group may be a terminal group or a bridging group.

"Alkyl" as a group or part of a group refers to a straight, linear or branched aliphatic hydrocarbon group, preferably a $C_1$-$C_{20}$ alkyl, more preferably a $C_2$-$C_{18}$ alkyl, most preferably $C_5$-$C_{16}$ unless otherwise noted. Examples of suitable straight and branched $C_1$-$C_6$ alkyl substituents include methyl, ethyl, n-propyl, 2-propyl, n-butyl, sec-butyl, t-butyl, hexyl, and the like. The group may be a terminal group or a bridging group.

"Alkynyl" as a group or part of a group means an aliphatic hydrocarbon group containing a carbon-carbon triple bond and which may be straight, linear or branched preferably having from 2-20 carbon atoms, more preferably 2-18 carbon atoms, more preferably 5-16 carbon atoms in the normal chain. Exemplary structures include, but are not limited to, ethynyl and propynyl. The group may be a terminal group or a bridging group.

"Amino acid" as a group or part of a group means having at least one primary, secondary, tertiary or quaternary amino group, and at least one acid group, wherein the acid group may be a carboxylic, sulfonic, or phosphonic acid, or mixtures thereof. The amino groups may be "alpha", "beta", "gamma" . . . to "omega" with respect to the acid group(s). The amino acid may be natural or synthetic, and may include their derivatives. The backbone of the "amino acid" may be substituted with one or more groups selected from halogen, hydroxy, guanido, heterocyclic groups. Thus the term "amino acids" also includes within its scope glycine, alanine, valine, leucine, isoleucine, methionine, proline, phenylalanine, tryptophane, serine, threonine, cysteine, tyrosine, asparagine, glutamine, asparte, glutamine, lysine, arginine and histidine, taurine, betaine, N-methylalanine etc. (L) and (D) forms of amino acids are included in the scope of this disclosure. Additionally, the amino acids suitable for use in the present disclosure may be derivatized to include amino acids that are hydroxylated, phosphorylated, sulfonated, acylated, and glycosylated, to name a few.

"Amino acid residue" refers to amino acid structures that lack a hydrogen atom of the amino group (—NH—CHR—COOH), or the hydroxy moiety of the carboxygroup (NH2-CHR—CO—), or both (—NH—CHR—CO—).

"Amino" refers to groups of the form $NR_aR_b$ wherein $R_a$ and $R_b$ are individually selected from the group including but not limited to hydrogen, optionally substituted alkyl, optionally substituted alkenyl, optionally substituted alkynyl, and optionally substituted aryl groups.

"Aminoalkyl" means an $NH_2$-alkyl- group in which the alkyl group is as defined herein. The group may be a terminal group or a bridging group. If the group is a terminal group it is bonded to the remainder of the molecule through the alkyl group.

"Aryl" as a group or part of a group denotes (i) an optionally substituted monocyclic, or fused polycyclic, aromatic carbocycle (ring structure having ring atoms that are all carbon) preferably having from 5 to 12 atoms per ring. Examples of aryl groups include phenyl, naphthyl, and the like; (ii) an optionally substituted partially saturated bicyclic aromatic carbocyclic moiety in which a phenyl and a $C_{5-7}$ cycloalkyl or $C_{5-7}$ cycloalkenyl group are fused together to form a cyclic structure, such as tetrahydronaphthyl, indenyl or indanyl. The group may be a terminal group or a bridging group. Typically an aryl group is a $C_6$-$C_{18}$ aryl group.

"Arylalkenyl" means an aryl-alkenyl- group in which the aryl and alkenyl are as defined herein. Exemplary arylalkenyl groups include phenylallyl. The group may be a terminal group or a bridging group. If the group is a terminal group it is bonded to the remainder of the molecule through the alkenyl group.

"Arylalkyl" means an aryl-alkyl- group in which the aryl and alkyl moieties are as defined herein. Preferred arylalkyl groups contain a $C_{1-5}$ alkyl moiety. Exemplary arylalkyl groups include benzyl, phenethyl, 1-naphthalenemethyl and 2-naphthalenemethyl. The group may be a terminal group or a bridging group. If the group is a terminal group it is bonded to the remainder of the molecule through the alkyl group.

"Arylheteroalkyl" means an aryl-heteroalkyl- group in which the aryl and heteroalkyl moieties are as defined herein. The group may be a terminal group or a bridging group. If the group is a terminal group it is bonded to the remainder of the molecule through the heteroalkyl group.

A "bond" is a linkage between atoms in a compound or molecule. The bond may be a single bond, a double bond, or a triple bond.

"Cycloalkenyl" means a non-aromatic monocyclic or multicyclic ring system containing at least one carbon-carbon double bond and preferably having from 5-10 carbon atoms per ring. Exemplary monocyclic cycloalkenyl rings include cyclopentenyl, cyclohexenyl or cycloheptenyl. The cycloalkenyl group may be substituted by one or more substituent groups. A cycloalkenyl group typically is a $C_3$-$C_{12}$ alkenyl group. The group may be a terminal group or a bridging group.

"Cycloalkyl" refers to a saturated monocyclic or fused or bridged or spiro polycyclic, carbocycle preferably containing from 3 to 9 carbons per ring, such as cyclopropyl, cyclobutyl, cyclopentyl, cyclohexyl and the like, unless otherwise specified. It includes monocyclic systems such as cyclopropyl and cyclohexyl, bicyclic systems such as decalin, and polycyclic systems such as adamantane. A cycloalkyl group typically is a $C_3$-$C_{12}$ alkyl group. The group may be a terminal group or a bridging group.

"Cycloalkylalkyl" means a cycloalkyl-alkyl- group in which the cycloalkyl and alkyl moieties are as defined herein. Exemplary monocycloalkylalkyl groups include cyclopropylmethyl, cyclopentylmethyl, cyclohexylmethyl and cycloheptylmethyl. The group may be a terminal group or a bridging group. If the group is a terminal group it is bonded to the remainder of the molecule through the alkyl group.

"Cycloalkylalkenyl" means a cycloalkyl-alkenyl- group in which the cycloalkyl and alkenyl moieties are as defined herein. The group may be a terminal group or a bridging group. If the group is a terminal group it is bonded to the remainder of the molecule through the alkenyl group.

"Cycloalkylheteroalkyl" means a cycloalkyl-heteroalkyl- group in which the cycloalkyl and heteroalkyl moieties are as defined herein. The group may be a terminal group or a bridging group. If the group is a terminal group it is bonded to the remainder of the molecule through the heteroalkyl group.

"Cycloamino" refers to a saturated monocyclic, bicyclic, or polycyclic ring containing at least one nitrogen in at least one ring. Each ring is preferably from 3 to 10 membered, more preferably 4 to 7 membered. The group may be a terminal group or a bridging group. If the group is a terminal group it is bonded to the remainder of the molecule through the nitrogen atom.

"Haloalkyl" refers to an alkyl group as defined herein in which one or more of the hydrogen atoms has been replaced with a halogen atom selected from the group consisting of fluorine, chlorine, bromine and iodine. A haloalkyl group typically has the formula $C_nH_{(2n+1-m)}X_m$ wherein each X is independently selected from the group consisting of F, Cl, Br and I. In groups of this type n is typically from 1 to 10, more preferably from 1 to 6, most preferably 1 to 3. m is typically 1 to 6, more preferably 1 to 3. Examples of haloalkyl include fluoromethyl, difluoromethyl and trifluoromethyl.

"Haloalkenyl" refers to an alkenyl group as defined herein in which one or more of the hydrogen atoms has been replaced with a halogen atom independently selected from the group consisting of F, Cl, Br and I.

"Haloalkynyl" refers to an alkynyl group as defined herein in which one or more of the hydrogen atoms has been replaced with a halogen atom independently selected from the group consisting of F, Cl, Br and I.

"Halogen" represents chlorine, fluorine, bromine or iodine.

"Heteroalkyl" refers to a straight-, linear- or branched-chain alkyl group preferably having from 2 to 12 carbons, more preferably 2 to 6 carbons in the chain, one or more of which has been replaced by a heteroatom selected from S, O, P and N. Exemplary heteroalkyls include alkyl ethers, secondary and tertiary alkyl amines, amides, alkyl sulfides, and the like. Examples of heteroalkyl also include hydroxyC$_1$-C$_6$alkyl, C$_1$-C$_6$alkyloxyC$_1$-C$_6$alkyl, aminoC$_1$-C$_6$alkyl, C$_1$-C$_6$ alkylaminoC$_1$-C$_6$alkyl, and di(C$_1$-C$_6$alkyl)aminoC$_1$-C$_6$alkyl. The group may be a terminal group or a bridging group.

"Heteroaryl" either alone or part of a group refers to groups containing an aromatic ring (preferably a 5 or 6 membered aromatic ring) having one or more heteroatoms as ring atoms in the aromatic ring with the remainder of the ring atoms being carbon atoms. Suitable heteroatoms include nitrogen, oxygen and sulphur. Examples of heteroaryl include thiophene, benzothiophene, benzofuran, benzimidazole, benzoxazole, benzothiazole, benzisothiazole, naphtho[2,3-b]thiophene, furan, isoindolizine, xantholene, phenoxatine, pyrrole, imidazole, pyrazole, pyridine, pyrazine, pyrimidine, pyridazine, tetrazole, indole, isoindole, 1H-indazole, purine, quinoline, isoquinoline, phthalazine, naphthyridine, quinoxaline, cinnoline, carbazole, phenanthridine, acridine, phenazine, thiazole, isothiazole, phenothiazine, oxazole, isooxazole, furazane, phenoxazine, 2-, 3- or 4-pyridyl, 2-, 3-, 4-, 5-, or 8-quinolyl, 1-, 3-, 4-, or 5-isoquinolinyl 1-, 2-, or 3-indolyl, and 2-, or 3-thienyl. A heteroaryl group is typically a $C_1$-$C_{18}$ heteroaryl group. A heteroaryl group may comprise 3 to 8 ring atoms. A heteroaryl group may comprise 1 to 3 heteroatoms independently selected from the group consisting of N, O and S. The group may be a terminal group or a bridging group.

"Heteroarylalkyl" means a heteroaryl-alkyl group in which the heteroaryl and alkyl moieties are as defined herein. Preferred heteroarylalkyl groups contain a lower alkyl moiety. Exemplary heteroarylalkyl groups include pyridylmethyl. The group may be a terminal group or a bridging group. If the group is a terminal group it is bonded to the remainder of the molecule through the alkyl group.

"Heteroarylalkenyl" means a heteroaryl-alkenyl- group in which the heteroaryl and alkenyl moieties are as defined herein. The group may be a terminal group or a bridging group. If the group is a terminal group it is bonded to the remainder of the molecule through the alkenyl group.

"Heteroarylheteroalkyl" means a heteroaryl-heteroalkyl-group in which the heteroaryl and heteroalkyl moieties are as defined herein. The group may be a terminal group or a bridging group. If the group is a terminal group it is bonded to the remainder of the molecule through the heteroalkyl group.

"Heteroarylamino" refers to groups containing an aromatic ring (preferably 5 or 6 membered aromatic ring) having at least one nitrogen and at least another heteroatom as ring atoms in the aromatic ring, preferably from 1 to 3 heteroatoms in at least one ring. Suitable heteroatoms include nitrogen, oxygen and sulphur. Arylamino and aryl is as defined herein. The group may be a terminal group or a bridging group. If the group is a terminal group it is bonded to the remainder of the molecule through the nitrogen atom.

"Heterocyclic" refers to saturated, partially unsaturated or fully unsaturated monocyclic, bicyclic or polycyclic ring system containing at least one heteroatom selected from the group consisting of nitrogen, sulfur and oxygen as a ring atom. Examples of heterocyclic moieties include heterocycloalkyl, heterocycloalkenyl and heteroaryl.

"Heterocycloalkenyl" refers to a heterocycloalkyl as defined herein but containing at least one double bond. A heterocycloalkenyl group typically is a $C_2$-$C_{12}$ heterocycloalkenyl group. The group may be a terminal group or a bridging group.

"Heterocycloalkyl" refers to a saturated monocyclic, fused or bridged or spiro polycyclic ring containing at least one heteroatom selected from nitrogen, sulfur, oxygen, preferably from 1 to 3 heteroatoms in at least one ring. Each ring is preferably from 3 to 10 membered, more preferably 4 to 7 membered. Examples of suitable heterocycloalkyl substituents include pyrrolidyl, tetrahydrofuryl, tetrahydrothiofuranyl, piperidyl, piperazyl, tetrahydropyranyl, morpholino, 1,3-diazapane, 1,4-diazapane, 1,4-oxazepane, and 1,4-oxathiapane. A heterocycloalkyl group typically is a $C_2$-$C_{12}$ heterocycloalkyl group. A heterocycloalkyl group may comprise 3 to 9 ring atoms. A heterocycloalkyl group may comprise 1 to 3 heteroatoms independently selected from the group consisting of N, O and S. The group may be a terminal group or a bridging group.

"Heterocycloalkylalkyl" refers to a heterocycloalkyl-alkyl- group in which the heterocycloalkyl and alkyl moieties are as defined herein. Exemplary heterocycloalkylalkyl groups include (2-tetrahydrofuryl)methyl, (2-tetrahydrothiofuranyl) methyl. The group may be a terminal group or a bridging group. If the group is a terminal group it is bonded to the remainder of the molecule through the alkyl group.

"Heterocycloalkylalkenyl" refers to a heterocycloalkyl-alkenyl- group in which the heterocycloalkyl and alkenyl moieties are as defined herein. The group may be a terminal group or a bridging group. If the group is a terminal group it is bonded to the remainder of the molecule through the alkenyl group.

"Heterocycloalkylheteroalkyl" means a heterocycloalkyl-heteroalkyl- group in which the heterocycloalkyl and heteroalkyl moieties are as defined herein. The group may be a terminal group or a bridging group. If the group is a terminal group it is bonded to the remainder of the molecule through the heteroalkyl group.

"Heterocycloamino" refers to a saturated monocyclic, bicyclic, or polycyclic ring containing at least one nitrogen and at least another heteroatom selected from nitrogen, sulfur, oxygen, preferably from 1 to 3 heteroatoms in at least one ring. Each ring is preferably from 3 to 10 membered, more preferably 4 to 7 membered. The group may be a terminal group or a bridging group. If the group is a terminal group it is bonded to the remainder of the molecule through the nitrogen atom.

"Hydroxyalkyl" refers to an alkyl group as defined herein in which one or more of the hydrogen atoms has been replaced with an OH group. A hydroxyalkyl group typically has the formula $C_nH_{(2n+1-x)}(OH)_x$ In groups of this type n is typically from 1 to 10, more preferably from 1 to 6, most preferably from 1 to 3. x is typically from 1 to 6, more preferably from 1 to 4.

"Lower alkyl" as a group means unless otherwise specified, an aliphatic hydrocarbon group which may be straight, linear or branched having 1 to 6 carbon atoms in the chain, more preferably 1 to 4 carbons such as methyl, ethyl, propyl (n-propyl or isopropyl) or butyl (n-butyl, isobutyl or tertiarybutyl). The group may be a terminal group or a bridging group.

"Patient," as used herein, refers to an animal, preferably a mammal, and most preferably a human.

"Subject" refers to a human or an animal.

It is understood that included in the family of compounds of Formula (I) are isomeric forms including diastereoisomers, enantiomers, tautomers, and geometrical isomers in "E" or "Z" configurational isomer or a mixture of E and Z isomers. It is also understood that some isomeric forms such as diastereomers, enantiomers, and geometrical isomers can be separated by physical and/or chemical methods and by those skilled in the art.

Some of the compounds of the disclosed embodiments may exist as single stereoisomers, racemates, and/or mixtures of enantiomers and/or diastereomers. All such single stereoisomers, racemates and mixtures thereof, are intended to be within the scope of the subject matter described and claimed.

Additionally, Formula (I) is intended to cover, where applicable, solvated as well as unsolvated forms of the compounds. Thus, each formula includes compounds having the indicated structure, including the hydrated as well as the non-hydrated forms.

Further, it is possible that compounds of the invention may contain more than one asymmetric carbon atom. In those compounds, the use of a solid line to depict bonds to asymmetric carbon atoms is meant to indicate that all possible stereoisomers are meant to be included. The use of a solid line to depict bonds to one or more asymmetric carbon atoms in a compound of the invention and the use of a solid or dotted wedge to depict bonds to other asymmetric carbon atoms in the same compound is meant to indicate that a mixture of diastereomers is present.

The term "optionally substituted" as used herein means the group to which this term refers may be unsubstituted, or may be substituted with one or more groups independently selected from alkyl, alkenyl, alkynyl, thioalkyl, cycloalkyl, cycloalkylalkyl, cycloalkenyl, cycloalkylalkenyl, heterocycloalkyl, cycloalkylheteroalkyl, cycloalkyloxy, cycloalkenyloxy, cycloamino, halo, carboxyl, haloalkyl, haloalkenyl, haloalkynyl, alkynyloxy, heteroalkyl, heteroalkyloxy, hydroxyl, hydroxyalkyl, alkoxy, thioalkoxy, alkenyloxy, haloalkoxy, haloalkenyloxy, nitro, amino, nitroalkyl, nitroalkenyl, nitroalkynyl, nitroheterocyclyl, alkylamino, dialkylamino, alkenylamine, aminoalkyl, alkynylamino, acyl, alkyloxy, alkyloxyalkyl, alkyloxyaryl, alkyloxycarbonyl, alkyloxycycloalkyl, alkyloxyheteroaryl, alkyloxyheterocycloalkyl, alkenoyl, alkynoyl, acylamino, diacylamino, acyloxy, alkylsulfonyloxy, heterocyclic, heterocycloalkenyl, heterocycloalkyl, heterocycloalkylalkyl, heterocycloalkylalkenyl, heterocycloalkylheteroalkyl, heterocycloalkyloxy, heterocycloalkenyloxy, heterocycloxy, heterocycloamino, haloheterocycloalkyl, alkylsulfinyl, alkylsulfonyl, alkylsulfenyl, alkylcarbonyloxy, alkylthio, acylthio, aminosulfonyl, phosphorus-containing groups such as phosphono and phosphinyl, sulfinyl, sulfinylamino, sulfonyl, sulfonylamino, aryl, heteroaryl, heteroarylalkyl, heteroarylalkenyl, heteroarylheteroalkyl, heteroarylamino, heteroaryloxy, arylalkenyl, arylalkyl, alkylaryl, alkylheteroaryl, aryloxy, arylsulfonyl, cyano, cyanate, isocyanate, —C(O)NH(alkyl), and —C(O)N(alkyl)$_2$.

Preferably, the alkyl is an optionally substituted $C_1$-$C_{20}$ alkyl, the alkenyl is an optionally substituted $C_1$-$C_{20}$ alkenyl, the alkynyl is a $C_1$-$C_{20}$ alkynyl, the thioalkyl is an optionally substituted $C_1$-$C_{20}$ thioalkyl comprising 1 or 2 sulfur atoms, the alkyloxy is an optionally substituted $C_1$-$C_6$ alkyl-O-group, the cycloalkyl is an optionally substituted $C_3$-$C_9$ cycloalkyl, the cycloalkylalkyl is an optionally substituted $C_3$ to $C_9$ cycloalkylalkyl, the cycloalkenyl is an optionally substituted $C_3$-$C_9$ cycloalkenyl, the cycloalkylalkenyl is an optionally substituted $C_3$ to $C_9$ cycloalkylalkenyl, the heterocycloalkyl is an optionally substituted heterocycloalkyl having a ring atom number of 3 to 8 and having 1 to 3 heteroatoms independently selected from the group consisting of N, O and S, the cycloalkylheteroalkyl is an optionally substituted cycloalkylheteroalkyl having a ring atom number of 3 to 8 and having 1 to 3 heteroatoms independently selected from the group consisting of N, O and S, the cycloalkoxy is an optionally substituted cycloalkoxy having a ring atom number of 3 to 8 and having 1 or 2 oxygen atoms, the cycloalkenyloxy is an optionally substituted cycloalkenyloxy having a ring atom number of 3 to 8 and having 1 or 2 oxygen atoms, the cycloamino is an optionally substituted cycloamino having a ring atom number of 3 to 8 and having 1 or 2 nitrogen atoms, halo is selected from the group consisting of fluoro, chloro, bromo and iodo, haloalkyl is an optionally substituted $C_1$-$C_{12}$ haloalkyl having at least one halo group selected from the group consisting of fluoro, chloro, bromo and iodo, haloalkenyl is an optionally substituted $C_1$-$C_{12}$ haloalkenyl having at least one halo group selected from the group consisting of fluoro, chloro, bromo and iodo, haloalkynyl is an optionally substituted $C_1$-$C_{12}$ haloalkynyl having at least one halo group selected from the group consisting of fluoro, chloro, bromo and iodo, alkenyloxy is an optionally substituted $C_1$-$C_6$ alkenyloxy having at least one oxygen atom, alkynyloxy is an optionally substituted $C_1$-$C_6$ alkynyloxy having at least one oxygen atom, heteroalkyl is an optionally substituted $C_2$-$C_{12}$ alkyl having a least one heteroatom selected from the group consisting of N, O, P and S, heteroalkyloxy is an optionally substituted $C_2$-$C_{12}$ alkyl having at least one oxygen atom and at least one other heteroatom selected from the group consisting of N, O, P and S, hydroxyalkyl is a substituted alkyl having the formula $C_nH_{(2n+1-x)}(OH)_x$ where n is 1 to 10, the thioalkyloxy is an optionally substituted $C_1$-$C_6$ alkyl-O— group having at least one sulfur group, the haloalkyloxy is an optionally substituted $C_1$-$C_6$ alkyl-O— group having at least one other substituent selected from the group consisting of fluoro, chloro, bromo and iodo, haloalkenyloxy is an optionally substituted $C_1$-$C_6$ alkenyloxy having at least one oxygen atom and at least one other substituent selected from the group consisting of fluoro, chloro, bromo and iodo, the nitroalkyl is an optionally substituted $C_1$-$C_{12}$ alkyl having at least one nitro group, the nitroalkenyl is an optionally substituted $C_1$-$C_{12}$ alkenyl having at least one nitro group, the nitroalkynyl is an optionally substituted $C_1$-$C_{12}$ alkynyl having at least one nitro group, the nitroheterocyclyl is an optionally substituted heterocycloalkyl having a ring atom number of 3 to 8 and having 1 to 3 heteroatoms independently selected from the group consisting of N, O and S and having at least one nitro group, the optionally substituted aryl is an optionally substituted $C_6$-$C_{18}$ aryl, the heteroaryl is an optionally substituted heteroaryl having a ring atom number of 3 to 8 and having 1 to 3 heteroatoms independently selected from the group consisting of N, O and S, alkylamino is an optionally substituted alkyl-NH— group having a $C_1$-$C_6$ alkyl group, dialkylamino is an optionally substituted (alkyl)$_2$N- group having a $C_1$-$C_6$ alkyl group, alkenylamine is an optionally substituted alkenyl-NH-group having a $C_1$-$C_6$ alkenyl group, alkynyl amino is an optionally substituted alkynyl-NH— group having a $C_1$-$C_6$ alkynyl group, alkyloxyalkyl is an optionally substituted alkyloxy group having a $C_1$-$C_6$ alkyl group, alkyloxyaryl is an optionally substituted alkyloxy group having an optionally substituted $C_6$-$C_{18}$ aryl, alkyloxycarbonyl is a an optionally substituted $C_1$-$C_{16}$ alkyloxy having a carbonyl group, alkyloxycyclocarbonyl is an optionally substituted optionally substituted $C_3$ to $C_9$ cycloalkylalkyl having a carbonyl group and an alkoxy group, the alkyloxyheteroaryl is an optionally substituted heteroaryl having a ring atom number of 3 to 8 and having 1 to 3 heteroatoms independently selected from the group consisting of N, O and S and having a $C_1$-$C_6$ alkyloxy group, alkyloxyheterocycloalkyl is an optionally substituted an optionally substituted heterocycloalkyl having a ring atom number of 3 to 8 and having 1 to 3 heteroatoms independently selected from the group consisting of N, O and S having a $C_1$-$C_6$ alkyloxy group, alkanoyl is an optionally substituted $C_1$-$C_{12}$ alkyl having a carbonyl group, alkenoyl is an optionally substituted $C_1$-$C_{12}$ alkenyl having a carbonyl group, alkynoyl is an optionally substituted $C_1$-$C_{12}$ alkynyl having a carbonyl group, acylamino is an optionally substituted R—C(=O)—NH— group in which the R group may be a $C_1$-$C_{12}$ alkyl, $C_3$-$C_{12}$ cycloalkyl, $C_3$-$C_{12}$ heterocycloalkyl having 1 to 3 heteroatoms independently selected from the group consisting of N, O and S, aryl having a ring atom number of 3 to 8 or heteroaryl group having a ring atom number of 3 to 8 and having 1 to 3 heteroatoms independently selected from the group consisting of N, O and S, diacylamino is an optionally substituted [R—C(=O)]$_2$ —NH group in which the R group may be a $C_1$-$C_{12}$ alkyl, $C_3$-$C_{12}$ cycloalkyl, $C_3$-$C_{12}$ heterocycloalkyl having 1 to 3 heteroatoms independently selected from the group consisting of N, O and S aryl having a ring atom number of 3 to 8 or heteroaryl group having a ring atom number of 3 to 8 and having 1 to 3 heteroatoms independently selected from the group consisting of N, O and S, the acyloxy is a $C_1$-$C_{12}$ acyloxy, the alkylsufonyloxy is an optionally substituted $C_1$-$C_6$ alkyl-O— group having at least one sulfonyl group, the heterocycloalkenyl is a heterocycloalkenyl having a ring atom number of 3 to 8 and having 1 to 3 heteroatoms independently selected from the group consisting of N, O and S, the heterocycloalkyl is a heterocycloalkyl having a ring atom number of 3 to 8 and having 1 to 3 heteroatoms independently selected from the group consisting of N, O and S, the heterocycloalkylalkyl is an optionally substituted $C_3$ to $C_9$ cycloalkylalkyl having 1 to 3 heteroatoms independently selected from the group consisting of N, O and S, the heterocycloalkylalkenyl is an optionally substituted $C_3$ to $C_9$ cycloalkylalkenyl having 1 to 3 heteroatoms independently selected from the group consisting of N, O and S, the heterocycloalkylheteroalkyl is an optionally substituted $C_3$ to $C_9$ cycloalkylalkenyl having 1 to 3 heteroatoms independently selected from the group consisting of N, O and S, the heterocycloalkyloxy is an optionally substituted $C_3$ to $C_9$ cycloalkyl having 1 to 3 heteroatoms independently selected from the group consisting of N, O and S and an optionally substituted $C_1$-$C_6$ alkyl-O— group, the heterocycloalkenyloxy is an optionally substituted $C_3$ to $C_9$ cycloalknyl having 1 to 3 heteroatoms independently selected from the group consisting of N, O and S and an optionally substituted $C_1$-$C_6$ alkyl-O— group, the heterocycloxy is an optionally substituted heterocycloalkyl having a ring atom number of 3 to 8 and having 1 to 3 heteroatoms independently selected from the group consisting of N, O and S and a hydroxyl group, the heterocycloamino is an optionally substituted heterocycloalkyl having a ring atom number of 3 to 8 and having 1 to 3 heteroatoms independently selected from the group consisting of N, O and S and an amino group, the haloheterocycloalkyl is an optionally substituted heterocycloalkyl having a ring atom number of 3 to 8 and having 1 to 3 heteroatoms independently selected from the group consisting of N, O and S and a halo group selected from the group consisting of fluoro, chloro, iodo and bromo, the alkylsufinyl is an optionally substituted $C_1$-$C_{12}$ alkyl group having at least one sulfinyl group, the alkylsufonyl is an optionally substituted $C_1$-$C_{12}$ alkyl group having at least one sulfonyl group, the alkylsufenyl is an optionally substituted $C_1$-$C_{12}$ alkyl group having at least one sulfenyl group, the alkylcarbonyloxy is an optionally substituted $C_1$-$C_{12}$ alkyl group having at least one carbonyl group and at least one hydroxy group, the alkylthio is an optionally substituted $C_1$-$C_{12}$ alkyl group having at least one thiol group, the acylthio is R—C(=O)—S in which R group may be a $C_1$-$C_{12}$ alkyl, $C_3$-$C_{12}$ cycloalkyl, $C_3$-$C_{12}$ heterocycloalkyl having 1 to 3 heteroatoms independently selected from the group consisting of N, O and S, aryl having a ring atom number of 3 to 8 or heteroaryl group having a ring atom number of 3 to 8 and having 1 to 3 heteroatoms independently selected from the group consisting of N, O and S, the heteroarylalkyl or alkylheteroaryl is an optionally substituted heteroaryl having a ring atom number of 3 to 8 and having 1 to 3 heteroatoms independently selected from the group consisting of N, O and S and a $C_1$-$C_{12}$ alkyl, the heteroarylalkenyl is an optionally substituted heteroaryl having a ring atom number of 3 to 8 and having 1 to 3 heteroatoms independently selected from the group consisting of N, O and S and a $C_1$-$C_{12}$ alkenyl, the heteroarylheteroalkyl is an optionally substituted heteroaryl having a ring atom number of 3 to 8 and having 1 to 3 heteroatoms independently selected from the group consisting of N, O and S and a $C_1$-$C_{12}$ alkyl having at least one heteroatom selected from the group consisting of N, O and S, the heteroarylamino is an optionally substituted heteroaryl having a ring atom number of 3 to 8 and having 1 to 3 heteroatoms independently selected from the group consisting of N, O and S and an amino group, the heteroaryloxy is an optionally substituted heteroaryl having a ring atom number of 3 to 8 and having at least one oxygen group, the arylalkenyl is an optionally substituted heteroaryl having a ring atom number of 3 to 8 and having 1 to 3 heteroatoms independently selected from the group consisting of N, O and S and a $C_1$-$C_{12}$ alkenyl, the arylalkyl or alkylaryl is an optionally substituted heteroaryl having a ring atom number of 3 to 8 and having 1 to 3 heteroatoms independently selected from the group consisting of N, O and S and a $C_1$-$C_{12}$ alkyl, the aryloxy is an optionally substituted heteroaryl having a ring atom number of 3 to 8 and having at least one oxygen atom, or the arylsulfonyl is an optionally substituted heteroaryl having a ring atom number of 3 to 8 and having at least one sulfur atom.

The term "pharmaceutically acceptable salts" refers to salts that retain the desired biological activity of the above-identified compounds, and include pharmaceutically acceptable acid addition salts and base addition salts. Suitable pharmaceutically acceptable acid addition salts of compounds of Formula (I) may be prepared from an inorganic acid or from an organic acid. Examples of such inorganic acids are hydrochloric, sulfuric, and phosphoric acid. Appropriate organic acids may be selected from aliphatic, cycloaliphatic, aromatic, heterocyclic carboxylic and sulfonic classes of organic acids, examples of which are formic, acetic, propionic, succinic, glycolic, gluconic, lactic, malic, tartaric, citric, fumaric, maleic, alkyl sulfonic, arylsulfonic. Additional information on pharmaceutically acceptable salts can be found in Remington's Pharmaceutical Sciences, 19th Edition, Mack Publishing Co., Easton, Pa. 1995. In the case of agents that are solids, it is understood by those skilled in the art that the inventive compounds, agents and salts may exist in different crystalline or polymorphic forms, all of which are intended to be within the scope of the present disclosure and specified formulae.

"Prodrug" means a compound that undergoes conversion to a compound of formula (I) within a biological system, usually by metabolic means (e.g. by hydrolysis, reduction or oxidation). For example an ester prodrug of a compound of formula (I) containing a hydroxyl group may be convertible by hydrolysis in vivo to the parent molecule. Suitable esters of compounds of formula (I) containing a hydroxyl group, are for example formates, acetates, citrates, lactates, tartrates, malonates, oxalates, salicylates, propionates, succinates, fumarates, maleates, methylene-bis-β-hydroxynaphthoates, gestisates, isethionates, di-p-toluoyltartrates, methanesulphonates, ethanesulphonates, benzenesulphonates, p-toluenesulphonates, cyclohexylsulphamates and quinates. As another example an ester prodrug of a compound of formula (I) containing a carboxy group may be convertible by hydrolysis in vivo to the parent molecule. (Examples of ester prodrugs are those described by F. J. Leinweber, Drug Metab. Res., 18:379, 1987). Similarly, an acyl prodrug of a compound of formula (I) containing an amino group may be convertible by hydrolysis in vivo to the parent molecule (Many examples of prodrugs for these and other functional groups, including amines, are described in Prodrugs: Challenges and Rewards (Parts 1 and 2); Ed V. Stella, R. Borchardt, M. Hageman, R. Oliyai, H. Maag and J Tilley; Springer, 2007)

The term "therapeutically effective amount" or "effective amount" is an amount sufficient to effect beneficial or desired clinical results. An effective amount can be administered in one or more administrations. An effective amount is typically sufficient to palliate, ameliorate, stabilize, reverse, slow or delay the progression of the disease state.

The word "substantially" does not exclude "completely" e.g. a composition which is "substantially free" from Y may be completely free from Y. Where necessary, the word "substantially" may be omitted from the definition of the invention.

Unless specified otherwise, the terms "comprising" and "comprise", and grammatical variants thereof, are intended to represent "open" or "inclusive" language such that they include recited elements but also permit inclusion of additional, unrecited elements.

As used herein, the term "about", in the context of concentrations of components of the formulations, typically means±10% of the stated value, more typically ±7.5% of the stated value, more typically ±5% of the stated value, more typically ±4% of the stated value, more typically ±3% of the stated value, more typically, ±2% of the stated value, even more typically ±1% of the stated value, and even more typically ±0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Certain embodiments may also be described broadly and generically herein. Each of the narrower species and sub-generic groupings falling within the generic disclosure also form part of the disclosure. This includes the generic description of the embodiments with a proviso or negative limitation removing any subject matter from the genus, regardless of whether or not the excised material is specifically recited herein.

BRIEF DESCRIPTION OF DRAWINGS

The accompanying drawings illustrate a disclosed embodiment and serves to explain the principles of the disclosed embodiment. It is to be understood, however, that the drawings are designed for purposes of illustration only, and not as a definition of the limits of the invention.

FIG. 1 is a scheme showing the general procedure for the synthesis of the compounds disclosed.

FIG. 2 is a graph showing the hemolytic properties of the compounds at lower concentrations (up to 1000 ppm).

FIG. 3 is a graph showing the relationships between log P, log $HC_{10}$ and MIC (GM in ppm).

FIG. 4 is a graph showing CMC determination in deionized water.

FIG. 5 is a graph showing storage modulus G' against frequency.

FIG. 6 is a graph showing viscosity against shear rate.

FIG. 7 refers to (A) an image of gels in n-butanol, (B) SEM image of the Compound 2 gel in n-butanol and (C) a proposed mechanism for their self-assemble process.

FIG. 8 is a compound of Formula (I).

DETAILED DESCRIPTION OF EMBODIMENTS

A compound has the following Formula (I):

[CHEM. 1]

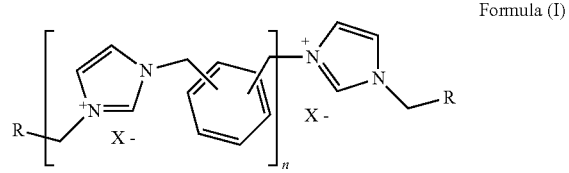

Formula (I)

wherein R may be an optionally substituted aliphatic group that is linear, cyclic, saturated, unsaturated or any combination thereof; n may be an integer of at least 1; and X may be an anionic counterion.

In an embodiment, R may be an optionally substituted linear alkyl, optionally substituted branched alkyl, optionally substituted cyclic alkyl, optionally substituted alkyl halide, optionally substituted alkyl alkene, optionally substituted alkyl alkyne or any combination thereof.

Preferably, R may be selected from the group consisting of optionally substituted saturated liner alkyl or optionally substituted saturated cyclic alkyl comprising 5 to 20 carbon atoms, and even more preferably 6 to 16 carbon atoms.

More preferably, R may be selected from the group consisting of saturated liner alkyl or saturated cyclic alkyl comprising 6 to 16 carbon atoms.

In an embodiment, R may be any isomer of an alkane selected from the group consisting of hexane, heptane, octane, nonane, decane, undecane, dodecane, tridecane, tetradecane, pentadecane, heptadecane, octadecane, nonadecane and eicosane.

In an embodiment, R may be selected from the group consisting of optionally substituted cyclopentylmethyl ($C_5H_9CH_2$), optionally substituted cyclohexylmethyl ($C_6H_{11}CH_2$), optionally substituted pentyl ($C_5H_{11}$), optionally substituted hexyl ($C_6H_{13}$), optionally substituted heptyl, ($C_7H_{15}$), optionally substituted octyl ($C_8H_{17}$), optionally substituted nonyl ($C_9H_{19}$), optionally substituted decyl ($C_{10}H_{21}$), optionally substituted undecyl ($C_{11}H_{23}$), optionally substituted dodecyl ($C_{12}H_{25}$), optionally substituted tridecyl ($C_{13}H_{17}$), optionally substituted tetradecyl ($C_{14}H_{29}$), optionally substituted pentadecyl ($C_{15}H_{31}$), optionally substituted hexadecyl ($C_{16}H_{33}$), optionally substituted heptadecyl ($C_{17}H_{35}$), optionally substituted octadecyl ($C_{18}H_{37}$), optionally substituted nonadecyl ($C_{19}H_{39}$), optionally substituted eicosyl ($C_{20}H_{41}$) and any mixture thereof.

In an embodiment, R may be selected from the group consisting of isopentyl, sec-pentyl, neopentyl, tert-pentyl, 2-methylpentyl, 3-methylpentyl, 2,2-dimetlybutyl, 2,3-dimethylbutyl, isohexyl, 2-methylhexyl, 3-methylhexyl, 2,2-dimethylpentyl, 2,3-dimethylpentyl, 2,4-dimethylpentyl, 3,3-dimethylpentyl, 3-ethylpentyl, 2,2,3-trimethylbutyl, 2-methylheptyl, 3-methylheptyl, 4-methylheptyl, 3-ethylhexyl, 2,2-dimethylhexyl, 2,3-dimethylhexyl, 2,4-dimethylhexyl, 2,5-dimethylhexyl, 3,3-dimethylhexyl, 3,4-dimethylhexyl, 3-ethyl-2-methylpentyl, 3-ethyl-3-methylpentyl, 2,2,3-trimethylpentyl, 2,2,4-trimethylpentyl, 2,2,3-trimethylpentyl, 2,3,4-trimethylpentyl, 2,3,3-trimethylpentyl, 2,3,4-trimethylpentyl, 2,2,3,3-tetramethylbutyl, 2,2-dimethylheptyl, 2,3-dimethylheptyl, 2,4-dimethylheptyl, 2,5-dimethylheptyl, 2,6-dimethylheptyl, 3,3-dimethylheptyl, 3,4-dimethylheptyl, 3,5-dimethylheptyl, 4,4-dimethylheptyl, 3-ethylheptyl, 4-ethylheptyl, 2,2,3-trimethylhexyl, 2,2,4-trimethylhexyl, 2,2,5-trimethylhexyl, 2,3,3,-trimethylhexyl, 2,3,4-trimethylhexyl, 2,3,5-trimethylhexyl, 2,4,4-trimethylhexyl, 3,34-trimethylhexyl, 3-ethyl-2-methylhexyl, 4-ethyl-2-methylhexyl, 3-ethyl-3-methylhexyl, 3-ethyl-4-methylhexyl, 2,2,3,3-tetramethylpentyl, 2,2,3,4-tetramethylpentyl, 2,2,4,4-tetramethylpentyl, 2,3,3,4-tetramethylpentyl, 3-ethyl-2,2-dimethylpentyl, 3-ethyl-2,3-dimethylpentyl, 3-ethyl-2,4-dimethylpentyl, 3-Isopropyl-2-methylhexyl, 2-Methyl-3-(1-methylethyl)hexyl, 3,3-Diethylhexyl, 3,4-Diethylhexyl, 3-Ethyl-2,2-dimethylhexyl, 3-Ethyl-2,3-dimethylhexyl, 3-Ethyl-2,4-dimethylhexyl, 3-Ethyl-2,5-dimethylhexyl, 3-Ethyl-3,4-dimethylhexyl, 4-Ethyl-2,2-dimethylhexyl, 4-Ethyl-2,3-dimethylhexyl, 4-Ethyl-2,4-dimethylhexyl, 4-Ethyl-3,3-dimethylhexyl, 2,2,3,3-Tetramethylhexyl, 2,2,3,4-Tetramethylhexyl, 2,2,3,5-Tetramethylhexyl, 2,2,4,4-Tetramethylhexyl, 2,2,4,5-Tetramethylhexyl, 2,2,5,5-Tetramethylhexyl, 2,3,3,4-Tetramethylhexyl, 2,3,3,5-Tetramethylhexyl, 2,3,4,4-Tetramethylhexyl, 2,3,4,5-Tetramethylhexyl, 3,3,4,4-Tetramethylhexyl, 3-Isopropyl-2,4-dimethylpentyl, 2,4-Dimethyl-3-(1-methylethyl)pentyl, 3,3-Diethyl-2-methylpentyl, 3-Ethyl-2,2,3-trimethylpentyl, 3-Ethyl-2,2,4-trimethylpentyl, 3-Ethyl-2,3,4-trimethylpentyl, 2,2,3,3,4-Pentamethylpentyl, 2,2,3,4,4-Pentamethylpentyl, 2-Methyldecyl, 3-Methyldecyl, 4-Methyldecyl, 5-Methyldecyl, 2,2-dimethylnonyl, 2,3-Dimethylnonyl, 2,4-Dimethylnonyl, 2,5-Dimethylnonyl, 2,6-Dimethylnonyl, 2,7-Dimethylnonyl, 2,8-Dimethylnonyl, 3,3-Dimethylnonyl, 3,4-Dimethylnonyl, 3,5-Dimethylnonyl, 3,6-Dimethylnonyl, 3,7-Dimethylnonyl, 4,4-Dimethylnonyl, 4,5-Dimethylnonyl, 4,6-Dimethylnonyl, 5,5-Dimethylnonyl, 3-Ethylnonyl, 4-Ethylnonyl, 5-Ethylnonyl, 2,2,3-Trimethyloctyl, 2,2,4-Trimethyloctyl, 2,2,5-Trimethyloctyl, 2,2,6-Trimethyloctyl, 2,2,7-Trimethyloctyl, 2,3,3-Trimethyloctyl, 2,3,4-Trimethyloctyl, 2,3,5-Trimethyloctyl, 2,3,6-Trimethyloctyl, 2,3,7-Trimethyloctyl, 2,4,4-Trimethyloctyl, 2,4,5-Trimethyloctyl, 2,4,6-Trimethylocty; 2,4,7-Trimethyloctyl, 2,5,5-Trimethyloctyl, 2,5,6-Trimethyloctyl, 2,6,6-Trimethyloctyl, 3,3,4-Trimethyloctyl, 3,3,5-Trimethyloctyl, 3,3,6-Trimethyloctyl, 3,4,4-Trimethyloctyl, 3,4,5-Trimethyloctyl, 3,4,6-Trimethyloctyl, 3,5,5-Trimethyloctyl, 4,4,5-Trimethyloctyl, 3-Ethyl-2-methyloctyl, 3-Ethyl-3-methyloctyl, 3-Ethyl-4-methyloctyl, 3-Ethyl-5-methyloctyl, 3-Ethyl-6-methyloctyl, 4-Ethyl-2-methyloctyl, 4-Ethyl-3-methyloctyl, 4-Ethyl-4-methyloctyl, 4-Ethyl-5-methyloctyl, 5-Ethyl-2-methyloctyl, 5-Ethyl-3-methyloctyl, 6-Ethyl-2-methyloctyl, 4-Propyloctyl, 4-(1-Methylethyl)octyl, 2,2,3,3-Tetramethylhepyl, 2,2,3,4-Tetramethylheptyl, 2,2,3,5-Tetramethylhepyl, 2,2,3,6-Tetramethylhepyl, 2,2,4,4-Tetramethylheptyl, 2,2,4,5-Tetramethylheptyl, 2,2,4,6-Tetramethylheptyl, 2,2,5,5-Tetramethylheptyl, 2,2,5,6-Tetramethylheptyl, 2,2,6,6-Tetramethylheptyl, 2,3,3,4-Tetramethylheptyl, 2,3,3,5-Tetramethylheptyl, 2,3,3,6-Tetramethylheptyl, 2,3,4,4-Tetramethylheptyl, 2,3,4,5-Tetramethylheptyl, 2,3,4,6-Tetramethylheptyl, 2,3,5,5-Tetramethylheptyl, 2,3,5,6-Tetramethylheptyl, 2,4,4,5-Tetramethylheptyl, 2,4,4,6-Tetramethylheptyl, 2,4,5,5-Tetramethylheptyl, 3,3,4,4-Tetramethylheptyl, 3,3,4,5-Tetramethylheptyl, 3,3,5,5-Tetramethylheptyl, 3,4,4,5-Tetramethylheptyl, 3-Ethyl-2,2-dimethylheptyl, 3-Ethyl-2,3-dimethylheptyl, 3-Ethyl-2,4-dimethylheptyl, 3-Ethyl-2,5-dimethylheptyl, 3-Ethyl-2,6-dimethylheptyl, 3-Ethyl-3,4-dimethylheptyl, 3-Ethyl-3,5-dimethylheptyl, 3-Ethyl-4,4-dimethylheptyl, 3-Ethyl-4,5-dimethylheptyl, 4-Ethyl-2,2-dimethylheptyl, 4-Ethyl-2,3-dimethylheptyl, 4-Ethyl-2,4-dimethylheptyl, 4-Ethyl-2,5-dimethylheptyl, 4-Ethyl-2,6-dimethylheptyl, 4-Ethyl-3,3-dimethylheptyl, 4-Ethyl-3,4-dimethylheptyl, 4-Ethyl-3,5-dimethylheptyl, 5-Ethyl-2,2-dimethylheptyl, 5-Ethyl-2,3-dimethylheptyl, 5-Ethyl-2,4-dimethylheptyl, 5-Ethyl-2,5-dimethylheptyl, 5-Ethyl-3,3-dimethylheptyl, 3,3-Diethylheptyl, 3,4-Diethylheptyl, 3,5-Diethylheptyl, 4,4-Diethylheptyl, 2-Methyl-4-propylheptyl, 3-Methyl-4-propylheptyl, 4-Methyl-4-propylheptyl, 2-Methyl-3-(1-methylethyl)heptyl, 2-Methyl-4-(1-methylethyl)heptyl, 3-Methyl-4-(1-methylethyl)heptyl, 4-Methyl-4-(1-methylethyl)heptyl, 4-(1, 1-Dimethylethyl)heptyl, 2,2,3,3,4-Pentamethylhexyl, 2,2,3,3,5-Pentamethylhexyl, 2,2,3,4,4-Pentamethylhexyl, 2,2,3,4,5-Pentamethylhexyl, 2,2,3,5,5-Pentamethylhexyl, 2,2,4,4,5-Pentamethylhexyl, 2,3,3,4,4-Pentamethylhexyl, 2,3,3,4,5-Pentamethylhexyl, 3-Ethyl-2,2,3-trimethylhexyl, 3-Ethyl-2,2,4-trimethylhexyl, 3-Ethyl-2,2,5-trimethylhexyl, 3-Ethyl-2,3,4-trimethylhexyl, 3-Ethyl-2,3,5-trimethylhexyl, 3-Ethyl-2,4,4-trimethylhexyl, 3-Ethyl-2,4,5-trimethylhexyl, 3-Ethyl-3,4,4-trimethylhexyl, 4-Ethyl-2,2,3-trimethylhexyl, 4-Ethyl-2,2,4-trimethylhexyl, 4-Ethyl-2,2,5-trimethylhexyl, 4-Ethyl-2,3,3-trimethylhexyl, 4-Ethyl-2,3,4-trimethylhexyl, 3,3-Diethyl-2-methylhexyl, 3,3-Diethyl-4-methylhexyl, 3,4-Diethyl-2-methylhexyl, 3,4-Diethyl-3-methylhexyl, 4,4-Diethyl-2-methylhexyl, 2,2-Dimethyl-3-(1-methylethyl)hexyl, 2,3-Dimethyl-3-(1-methylethyl)hexyl, 2,4-Dimethyl-3-(1-methylethyl)hexyl, 2,5-

Dimethyl-3-(1-methylethyl)hexyl, 2,2,3,3,4,4-Hexamethylpentyl, 3-Ethyl-2,2,3,4-tetramethylpentyl, 3-Ethyl-2,2,4,4-tetramethylpentyl, 3,3-Diethyl-2,2-dimethylpentyl, 3,3-Diethyl-2,4-dimethylpentyl, 2,2,4-Trimethyl-3-(1-methylethyl)pentyl, 2,3,4-Trimethyl-3-(1-methylethyl)pentyl, 2-Methylundecyl, 3-Methylundecyl, 4-Methylundecyl, 5-Methylundecyl, 6-Methylundecyl, 2,2-Dimethyldecyl, 2,3-Dimethyldecyl, 2,4-Dimethyldecyl, 2,5-Dimethyldecyl, 2,6-Dimethyldecyl, 2,7-Dimethyldecyl, 2,8-Dimethyldecyl, 2,9-Dimethyldecyl, 3,3-Dimethyldecyl, 3,4-Dimethyldecyl, 3,5-Dimethyldecyl, 3,6-Dimethyldecyl, 3,7-Dimethyldecyl, 3, 8-Dimethyldecyl, 4,4-Dimethyldecyl, 4,5-Dimethyldecyl, 4,6-Dimethyldecyl, 4,7-Dimethyldecyl, 5,5-Dimethyldecyl, 5,6-Dimethyldecyl, 3-Ethyldecyl, 4-Ethyldecyl, 5-Ethyldecyl, 2,2,3-Trimethylnonyl, 2,2,4-Trimethylnonyl, 2,2,5-Trimethylnonyl, 2,2,6-Trimethylnonyl, 2,2,7-Trimethylnonyl, 2,2,8-Trimethylnonyl, 2,3,3-Trimethylnonyl, 2,3,4-Trimethylnonyl, 2,3,5-Trimethylnonyl, 2,3,6-Trimethylnonyl, 2,3,7-Trimethylnonyl, 2,3, 8-Trimethylnonyl, 2,4,4-Trimethylnonyl, 2,4,5-Trimethylnonyl, 2,4,6-Trimethylnonyl, 2,4,7-Trimethylnonyl, 2,4,8-Trimethylnonyl, 2,5,5-Trimethylnonyl, 2,5,6-Trimethylnonyl, 2,5,7-Trimethylnonyl, 2,5,8-Trimethylnonyl, 2,6,6-Trimethylnonyl, 2,6,7-Trimethylnonyl, 2,7,7-Trimethylnonyl, 3,3,4-Trimethylnonyl, 3,3,5-Trimethylnonyl, 3,3,6-Trimethylnonyl, 3,3,7-Trimethylnonyl, 3,4,4-Trimethylnonyl, 3,4,5-Trimethylnonyl, 3,4,6-Trimethylnonyl, 3,4,7-Trimethylnonyl, 3,5,5-Trimethylnonyl, 3,5,6-Trimethylnonyl, 3,5,7-Trimethylnonyl, 3,6,6-Trimethylnonyl, 4,4,5-Trimethylnonyl, 4,4,6-Trimethylnonyl, 4,5,5-Trimethylnonyl, 4,5,6-Trimethylnonyl, 3-Ethyl-2-methylnonyl, 3-Ethyl-3-methylnonyl, 2,2,3,3-Tetramethyloctyl, 2,2,3,4-Tetramethyloctyl, 2,2,3,5-Tetramethyloctyl, 2,2,3,6-Tetramethyloctyl, 2,2,3,7-Tetramethyloctyl, 2,2,4,4-Tetramethyloctyl, 2,2,4,5-Tetramethyloctyl, 2,2,4,6-Tetramethyloctyl, 2,2,4,7-Tetramethyloctyl, 2,2,5,5-Tetramethyloctyl, 2,2,5,6-Tetramethyloctyl, 2,2,5,7-Tetramethyloctyl, 2,2,6,6-Tetramethyloctyl, 2,2,6,7-Tetramethyloctyl, 2,2,7,7-Tetramethyloctyl, 2,3,3,4-Tetramethyloctyl, 2,3,3,5-Tetramethyloctyl, 2,3,3,6-Tetramethyloctyl, 2,3,3,7-Tetramethyloctyl, 2,3,4,4-Tetramethyloctyl, 2,3,4,5-Tetramethyloctyl, 2,3,4,6-Tetramethyloctyl, 2,3,4,7-Tetramethyloctyl, 2,3,5,5-Tetramethyloctyl, 2,3,5,6-Tetramethyloctyl, 2,3,5,7-Tetramethyloctyl, 2,3,6,6-Tetramethyloctyl, 2,3,6,7-Tetramethyloctyl, 2,4,4,5-Tetramethyloctyl, 2,4,4,6-Tetramethyloctyl, 2,4,4,7-Tetramethyloctyl, 2,4,5,5-Tetramethyloctyl, 2,4,5,6-Tetramethyloctyl, 2,4,5,7-Tetramethyloctyl, 2,4,6,6-Tetramethyloctyl, 2,5,5,6-Tetramethyloctyl, 2,5,6,6-Tetramethyloctyl, 3,3,4,4-Tetramethyloctyl, 3,3,4,5-Tetramethyloctyl, 3,3,4,6-Tetramethyloctyl, 3,3,5,5-Tetramethyloctyl; 3,3,5,6-Tetramethyloctyl; 3,3,6,6-Tetramethyloctyl, 3,4,4,5-Tetramethyloctyl, 3,4,4,6-Tetramethyloctyl, 3,4,5,5-Tetramethyloctyl, 3,4,5,6-Tetramethyloctyl, 4,4,5,5-Tetramethyloctyl, 3-Ethyl-2,2-dimethyloctyl, 3-Ethyl-2,3-dimethyloctyl, 3-Ethyl-2,4-dimethyloctyl, 3-Ethyl-2,5-dimethyloctyl, 3-Ethyl-2,6-dimethyloctyl; 3-Ethyl-2,7-dimethyloctyl, 3-Ethyl-3,4-dimethyloctyl, 3-Ethyl-3,5-dimethyloctyl, 3-Ethyl-3,6-dimethyloctyl, 3-Ethyl-4,4-dimethyloctyl, 3-Ethyl-4,5-dimethyloctyl, 3-Ethyl-4,6-dimethyloctyl, 3-Ethyl-5,5-dimethyloctyl, 4-Ethyl-2,2-dimethyloctyl, 4-Ethyl-2,3-dimethyloctyl, 4-Ethyl-2,4-dimethyloctyl, 4-Ethyl-2,5-dimethyloctyl, 4-Ethyl-2,6-dimethyloctyl, 4-Ethyl-2,7-dimethyloctyl, 4-Ethyl-3,3-dimethyloctyl, 4-Ethyl-3,4-dimethyloctyl, 4-Ethyl-3,5-dimethyloctyl, 4-Ethyl-3,6-dimethyloctyl, 4-Ethyl-4,5-dimethyloctyl, 2,2,3,3,4-Pentamethylheptyl, 2,2,3,3,5-Pentamethylheptyl, 2,2,3,3,6-Pentamethylheptyl, 2,2,3,4,4-Pentamethylheptyl, 2,2,3,4,5-Pentamethylheptyl, 2,2,3,4,6-Pentamethylheptyl, 2,2,3,5,5-Pentamethylheptyl, 2,2,3,5,6-Pentamethylheptyl, 2,2,3,6,6-Pentamethylheptyl, 2,2,4,4,5-Pentamethylheptyl, 2,2,4,4,6-Pentamethylheptyl, 2,2,4,5,5-Pentamethylheptyl, 2,2,4,5,6-Pentamethylheptyl, 2,2,4,6,6-Pentamethylheptyl, 2,2,5,5,6-Pentamethylheptyl, 2,3,3,4,4-Pentamethylheptyl, 2,3,3,4,5-Pentamethylheptyl, 2,3,3,4,6-Pentamethylheptyl, 2,3,3,5,5-Pentamethylheptyl, 2,3,3,5,6-Pentamethylheptyl, 2,3,4,4,5-Pentamethylheptyl, 2,3,4,4,6-Pentamethylheptyl, 2,3,4,5,5-Pentamethylheptyl, 2,3,4,5,6-Pentamethylheptyl, 2,4,4,5,5-Pentamethylheptyl, 3,3,4,4,5-Pentamethylheptyl, 3,3,4,5,5-Pentamethylheptyl, 3-Ethyl-2,2,3-trimethylheptyl, 3-Ethyl-2,2,4-trimethylheptyl, 3-Ethyl-2,2,5-trimethylheptyl, 3-Ethyl-2,2,6-trimethylheptyl, 3-Ethyl-2,3,4-trimethylheptyl, 3-Ethyl-2,3,5-trimethylhepyl, 3-Ethyl-2,3,6-trimethylheptyl, 3-Ethyl-2,4,4-trimethylheptyl, 3-Ethyl-2,4,5-trimethylheptyl, 3-Ethyl-2,4,6-trimethylheptyl, 3-Ethyl-2,5,5-trimethylheptyl, 3-Ethyl-2,5,6-trimethylheptyl, 3-Ethyl-3,4,4-trimethylheptyl, 3-Ethyl-3,4,5-trimethylheptyl, 3-Ethyl-3,5,5-trimethylheptyl, 3-Ethyl-4,4,5-trimethylheptyl, 4-Ethyl-2,2,3-trimethylheptyl, 4-Ethyl-2,2,4-trimethylheptyl, 4-Ethyl-2,2,5-trimethylheptyl, 4-Ethyl-2,2,6-trimethylheptyl, 4-Ethyl-2,3,3-trimethylheptyl, 4-Ethyl-2,3,4-trimethylheptyl, 4-Ethyl-2,3,5-trimethylheptyl, 4-Ethyl-2,3,6-trimethylheptyl, 4-Ethyl-2,4,5-trimethylheptyl, 4-Ethyl-2,4,6-trimethylheptyl, 4-Ethyl-2,5,5-trimethylheptyl, 4-Ethyl-3,3,4-trimethylheptyl, 4-Ethyl-3,3,5-trimethylheptyl, 4-Ethyl-3,4,5-trimethylheptyl, 5-Ethyl-2,2,3-trimethylheptyl, 5-Ethyl-2,2,4-trimethylheptyl, 5-Ethyl-2,2,5-trimethylheptyl, 5-Ethyl-2,2,6-trimethylheptyl, 5-Ethyl-2,3,3-trimethylheptyl, 5-Ethyl-2,3,4-trimethylheptyl, 5-Ethyl-2,3,5-trimethylheptyl, 5-Ethyl-2,4,4-trimethylheptyl, 5-Ethyl-2,4,5-trimethylheptyl, 5-Ethyl-3,3,4-trimethylheptyl, 3,3-Diethyl-2-methylheptyl, 3,3-Diethyl-4-methylheptyl, 3,3-Diethyl-5-methylheptyl, 3,4-Diethyl-2-methylheptyl, 3,4-Diethyl-3-methylheptyl, 2,2,3,3,4,4-Hexamethylhexyl, 2,2,3,3,4,5-Hexamethylhexyl, 2,2,3,3,5,5-Hexamethylhexyl, 2,2,3,4,4,5-Hexamethylhexyl, 2,2,3,4,5,5-Hexamethylhexyl, 2,3,3,4,4,5-Hexamethylhexyl, 3-Ethyl-2,2,3,4-tetramethylhexyl, 3-Ethyl-2,2,3,5-tetramethylhexyl, 3-Ethyl-2,2,4,4-tetramethylhexyl, 3-Ethyl-2,2,4,5-tetramethylhexyl, 3-Ethyl-2,2,5,5-tetramethylhexyl, 3-Ethyl-2,3,4,4-tetramethylhexyl, 3-Ethyl-2,3,4,5-tetramethylhexyl, 4-Ethyl-2,2,3,3-tetramethylhexyl, 4-Ethyl-2,2,3,4-tetramethylhexyl, 4-Ethyl-2,2,3,5-tetramethylhexyl, 4-Ethyl-2,2,4,5-tetramethylhexyl, 4-Ethyl-2,3,3,4-tetramethylhexyl, 4-Ethyl-2,3,3,5-tetramethylhexyl, 3,3-Diethyl-2,2-dimethylhexyl, 3,3-Diethyl-2,4-dimethylhexyl, 3,3-Diethyl-2,5-dimethylhexyl; 3,3-Diethyl-4,4-dimethylhexyl, 3,4-Diethyl-2,2-dimethylhexyl, 3,4-Diethyl-2,3-dimethylhexyl, 3,4-Diethyl-2,4-dimethylhexyl, 3,4-Diethyl-2,5-dimethylhexyl, 3,4-Diethyl-3,4-dimethylhexyl, 3-Ethyl-2,2,3,4,4-pentamethylpentyl, 3,3-Diethyl-2,2,4-trimethylpentyl, 2,2,3,4-Tetramethyl-3-(1-methylethyl)pentyl, 2,2,4,4-Tetramethyl-3-(1-methylethyl)pentyl, and 3-Ethyl-2,4-dimethyl-3-(1-methylethyl)pentyl.

In an embodiment, R may be selected from the group consisting of optionally substituted cyclopentenylmethyl, optionally substituted cyclohexenylmethyl, optionally substituted pentenyl, optionally substituted hexenyl, optionally substituted heptenyl, optionally substituted octenyl, optionally substituted nonenyl, optionally substituted decenyl, optionally substituted undecenyl, optionally substituted dodecenyl, optionally substituted tridecenyl, optionally substituted tetradecenyl, optionally substituted pentadecenyl, optionally substituted hexadecenyl, optionally substituted heptadecenyl, optionally substituted octadecenyl, optionally substituted nonadecenyl, optionally substituted eicosenyl and any mixture thereof.

In an embodiment, R may be selected from the group consisting of optionally substituted cyclopentynylmethyl, optionally substituted cyclohexynylmethyl, optionally substituted pentynyl, optionally substituted hexynyl, optionally substituted heptynyl, optionally substituted octynyl, optionally substituted nonynyl, optionally substituted decynyl, optionally substituted undecynyl, optionally substituted dodecynyl, optionally substituted tridecynyl, optionally substituted tetradecynyl, optionally substituted pentadecynyl, optionally substituted hexadecynyl, optionally substituted heptadecynyl, optionally substituted octadecynyl, optionally substituted nonadecynyl, optionally substituted eicosynyl and any mixture thereof.

For instances where R is an optionally substituted alkenyl or optionally substituted alkynyl, the double bond or the triple bond, respectively, may appear one or more times in the chain. For instances where R is an optionally substituted alkenyl or optionally substituted alkynyl, the double bond or the triple bond, respectively, may appear at any position within the chain.

In an embodiment, R may be selected from the group consisting of cyclohexylmethyl ($C_6H_{11}CH_2$), hexyl ($C_6H_{13}$), octyl ($C_8H_{17}$), decyl ($C_{10}H_{21}$), dodecyl ($C_{12}H_{25}$), tetradecyl ($C_{14}H_{29}$), hexadecyl ($C_{16}H_{33}$) and any mixture thereof.

In an embodiment, n may be an integer selected from 1 to 10. In another embodiment, n may be 5, 6 or 7.

In another embodiment, X may be halogen, carbonate, phosphate, nitrate, sulfate, carboxylate or any combination thereof.

In another embodiment, the benzene ring in Formula (I) may be substituted at the meta-position, ortho-position, para-position or any combination thereof. In a preferred embodiment, the benzene ring in Formula (I) may be substituted at the meta-position. In a preferred embodiment, the benzene ring in Formula (I) may be substituted at the para-position.

In an embodiment, where there are multiple benzene rings in the compound as defined by Formula (I), then the benzene rings may independently be substituted at the meta-position, ortho-position, para-position or any combination thereof.

In yet another embodiment, the compound has the following Formula (II):

($C_8H_{17}$), decyl ($C_{10}H_{21}$), dodecyl ($C_{12}H_{25}$), tetradecyl ($C_{14}H_{29}$), hexadecyl ($C_{16}H_{33}$) and any mixture thereof.

In an embodiment, the compound may be amphiphilic. The amphiphilicity may be due to the presence of both a hydrophilic group (quaternary ammonium salts) and lipophilic group (amphiphilic group). Advantageously, the compound as described above may be amphiphilic because the hydrophilic groups are in the centre of the molecule, which are flanked by hydrophobic groups on the outer side of the molecule.

Advantageously, the compound may be an antimicrobial peptide (AMP)-mimicking imidazolium main-chain polymer that has antibiotic characteristics. More advantageously, the AMP-mimicking imidazolium polymer may exhibit selective membrane-disruptive activity, demonstrating a fast killing mechanism of microorganisms and the potential to deal with drug resistance issues usually associated with conventional antibiotics.

More advantageously, the compound as defined above may have structural characteristics that may be a fine balance of charge, due to attachment of quaternary ammonium salts, and hydrophobicity, due to the presence of long alkyl chains. This may in turn ascertain their efficacy and selectivity as an antimicrobial agent. By tuning the R substituents and hence the amphiphilic structure, the novel imidazolium compounds may demonstrate ultra-efficient antimicrobial activity over a broad-spectrum of microorganisms, where instant and selective bacterial kill (99.999% killing at the minimum inhibitory concentration (MIC)) is achieved, while preventing hemolysis, even at higher concentrations.

The compound as defined above may have vast structural diversity that may be obtained by multi-step organic synthesis for ease of tuning the final amphiphilicity of the polymer. This may in turn dictate the selectivity and efficacy of the compound as an antibiotic.

In a second aspect, there is provided a pharmaceutical composition comprising a compound as defined above, or a pharmaceutically acceptable salt or hydrate thereof, in association with a pharmaceutically acceptable carrier. The pharmaceutically acceptable carrier may be water or saline.

Advantageously, the compound as defined above has superior antibiotic activity while no effect on higher organisms. It may therefore be suitable for use in vivo.

In a third aspect, there is provided a gel comprising the compound as defined above and a solvent.

In an embodiment, the gel may be formed by self-assembly of the compound as defined above.

[CHEM. 2]

Formula (II)

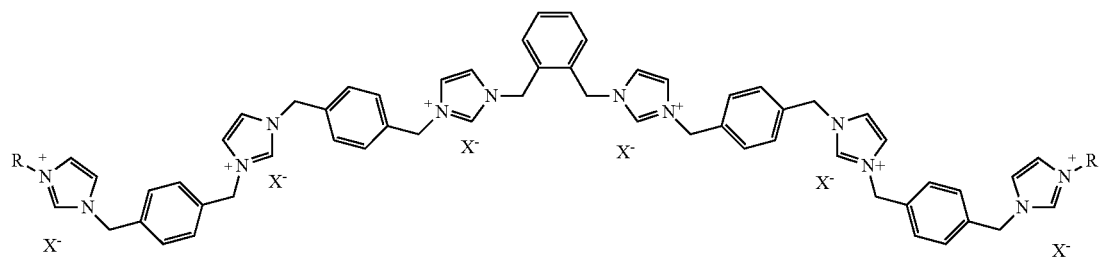

wherein R may be selected from the group consisting of cyclohexylmethyl ($C_6H_{11}CH_2$), hexyl ($C_6H_{13}$), octyl The solvent may be selected from the group consisting of water, ethylene glycol, glycerol, alcohol and any mixture thereof. In an embodiment, the solvent may be an alcohol. In an embodiment, the solvent may be a mixture of alcohol with water. The alcohol may be selected from the group consisting of methanol, ethanol, 1-propanol, 2-propanol, 1-butanol, 2-butanol, iso-butanol, tert-butanol, 1-pentanol, 2-pentanol 3-pentanol, 1-hexanol, 2-hexanol, 3-hexanol, 1-heptanol, 2-heptanol, 3-heptanol, 4-heptanol, 1-octanol, 2-octanol, 3-octanol and 4-octanol.

In another embodiment, the gel may comprise the compound as defined above in the range of about 4% to about 15% by weight, about 4% to about 6% by weight, about 4% to about 8% by weight, about 4% to about 10% by weight, about 4% to about 12% by weight, about 4% to about 14% by weight, about 4% to about 16% by weight, about 6% to about 8% by weight, about 6% to about 10% by weight, about 6% to about 12% by weight, about 6% to about 14% by weight, about 6% to about 16% by weight, about 8% to about 10% by weight, about 8% to about 12% by weight, about 8% to about 14% by weight, about 8% to about 16% by weight, about 10% to about 12% by weight, about 10% to about 14% by weight, about 10% to about 16% by weight, about 12% to about 14% by weight, about 12% to about 16% by weight or about 14% to about 16% by weight.

In an embodiment, the gel may be thixotropic.

Advantageously, the compound as defined above may be able to self-assemble to form gels in alcohols due to the well-balanced amphiphilic structure. More advantageously, the gels may be stable at ambient temperatures, and may be thixotropic. The gels may be weak gels that may be fluid matrix organogels in which the only forces holding them together are simple chain entanglements. As most existing amphiphilic antimicrobial materials can only form by triggering with a co-gelation polymer or grafting antimicrobial material with other copolymers, the compound as defined above has the advantageous property that it may self-assemble to form a gel.

In a fourth aspect, there is provided a use of the compound as defined above, the pharmaceutical composition as defined above or the gel as defined above, as an antibiotic.

In a fifth aspect, there is provided a use of the compound as defined above, the pharmaceutical composition as defined above or the gel as defined above, to kill or inhibit the growth of a microorganism.

In an embodiment, the microorganism may be is a bacterium, archaea, fungus, protist, animal, plant, or any mixture thereof.

Advantageously, the compound as defined above, the pharmaceutical composition as defined above or the gel as defined above may be used as an antibiotic or to kill or inhibit the growth of a microorganism. The compound, its pharmaceutical composition or its gel may have ultra-efficient antimicrobial activity over a broad-spectrum of microorganisms, where instant and selective bacterial kill (99.999% killing at the minimum inhibitory concentration (MIC)) may be achieved, while preventing hemolysis, even at higher concentrations. More advantageously, this may result in the use of the compound, pharmaceutical composition or gel in applications for sterilization, including antimicrobial handrubs and surface treatments.

In a sixth aspect, there is provided a method for synthesizing the gel as defined above, comprising the steps of:
  providing the compound as defined above;
  adding a solvent; and
  mixing the compound and the solvent;
  provided that an additional gelation-initiator is not added to the mixture.

In a seventh aspect, there is provided a method for synthesizing the gel as defined above, consisting the steps of:
  providing the compound as defined above;
  adding a solvent; and
  mixing the compound and the solvent.

The solvent may be selected from ethylene glycol, glycerol, or alcohol. In an embodiment, the solvent may be an alcohol. The alcohol may be selected from the group consisting of methanol, ethanol, 1-propanol, 2-propanol, 1-butanol, 2-butanol, iso-butanol, tert-butanol, 1-pentanol, 2-pentanol, 3-pentanol, 1-hexanol, 2-hexanol, 3-hexanol, 1-heptanol, 2-heptanol, 3-heptanol, 4-heptanol, 1-octanol, 2-octanol, 3-octanol and 4-octanol.

The mixing step may comprise vortexing or sonication.

Advantageously, the method for synthesizing the gel does not require the addition of co-gelation polymer or grafting of copolymers to initiate the gelling process.

EXAMPLES

Non-limiting examples of the disclosure will be further described in greater detail by reference to specific Examples, which should not be construed as in any way limiting the scope of the invention.

Example 1

Representative Compounds

[CHEM. 2]

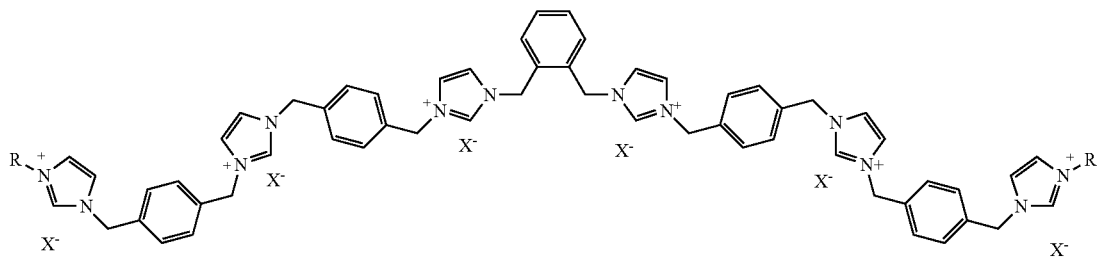

TABLE 1

List of R groups for the representative compounds

| Compound name | R |
|---|---|
| IBN-1 | $C_6H_5CH_2$ |
| Compound 1 | $C_6H_{13}$ |

TABLE 1-continued

List of R groups for the representative compounds

| Compound name | R |
|---|---|
| Compound 2 | $C_8H_{17}$ |
| Compound 3 | $C_{10}H_{21}$ |
| Compound 4 | $C_{12}H_{25}$ |
| Compound 5 | $C_{14}H_{29}$ |
| Compound 6 | $C_{16}H_{33}$ |
| Compound 7 | $C_6H_{11}CH_2$ |

As shown in the above structure, the end group R of the imidazolium oligomer compound is a cyclohexylmethyl (Cy) (Compound 7) or a linear n-alkyl (n=6 to 16, Compounds 1 to 6).

Example 2

Synthesis of the Imidazolium Oligomer Compounds

All materials were purchased from Sigma Aldrich or Merck, and used as purchased. All manipulations were done without any special precautions to eliminate air or moisture. Nuclear magnetic resonance (NMR) spectra were obtained using a Bruker AV-400 (400 MHz) spectrometer. Chemical shifts were reported in ppm from tetramethylsilane with the solvent resonance as the internal standard.

Synthesis of imidazolium oligomer compounds were adapted from protocols reported previously in L. Liu, Y. Huang, S. N. Riduan, S. Gao, Y.-Y Yang, W. Fan, Y. Zhang, *Biomaterials*, 2012, 33, 8525-8631; L. Liu, H. Wu, S. N. Riduan, Y. Zhang, J. Y. Ying, *Biomaterials*, 2013, 34, 1018-1023 and Y. Zhang, L. Zhao, P. K. Patra, D. Hu, J. Y. Ying, *Nano Today*, 2009, 4, 13-20. A representative scheme showing the synthesis of the compounds is shown in FIG. 1.

Representative synthesis of
1,4-bis(N-imidazole-1-ylmethyl)benzene (1)

A mixture of imidazole (0.9 g, 13.0 mmol) and sodium hydroxide (0.5 g, 12 mmol) in DMSO (5 mL) was heated to 90° C. for 2 h, and then was cooled to room temperature. A solution of α,α'-dichloro-p-xylene (0.99 g, 5.7 mmol) in DMSO (10 mL) was added to the mixture and heated slowly to 40° C. for 1 h with constant stirring. The solution obtained was poured into ice-cold water (40 mL). The precipitate was collected, washed with water, and recrystallized from methanol/water to give 1,4-bis(N-imidazole-1-ylmethyl) benzene (1) as a white solid (0.95 g, 79%). $^1$H NMR (CDCl$_3$): δ 7.55 (s, 2H), 7.13 (s, 4H), 7.10 (s, 2H), 6.89 (s, 2H), 5.12 (s, 4H). MS (GC-MS) m/z 238 (M+).

A similar procedure was used for the synthesis of 1,2-bis (N-imidazole-1-ylmethyl)benzene, α,α'-dichloro-o-xylylene (2). $^1$H NMR (CDCl$_3$): δ 7.45 (s, 2H), 7.38 (d, 2H), 7.12 (s, 2H), 7.08 (d, 2H), 6.80 (s, 2H), 5.03 (s, 4H). MS (GC-MS) m/z 238 (M$^+$).

Synthesis of Intermediate (3)

(3)-C6 is 1,4-bis(N-imidazole-1-ylmethyl)benzene (1) with a $C_6H_{13}$ substituent at one of the imidazole nitrogens, as represented by (3) in FIG. 1). A mixture of 1,4-bis(N-imidazole-1-ylmethyl)benzene (1) (10 mmol, 2.38 g) and 1-bromohexane (9.8 mmol, 1.375 mL) was stirred in DMF (15 mL) at 90° C. After overnight stirring, the reaction mixture was allowed to cool before pouring into diethyl ether (50 mL) to isolate the product as a viscous solution. Washing the viscous solution and drying the solution in vacuo to remove DMF would yield the product in quantitative yields. $^1$H NMR (DMSO-D6): δ 9.43 (s, 1H), 7.85 (m, 3H), 7.42 (d, 2H), 7.30 (d, 2H), 7.19 (s, 1H), 6.87 (s, 1H), 5.45 (s, 2H), 5.22 (s, 2H), 4.18 (m, 2H), 1.77 (b, 2H), 1.23 (b, 6H), 0.83 (t, 3H).

The same procedure was used to synthesize the compounds (3)-C8, (3)-C10, (3)-C12, (3)-C14 and (3)-C16 (1,4-bis(N-imidazole-1-ylmethyl)benzene (1) with a $C_8H_{12}$, $C_{10}H_{21}$, $C_{12}H_{25}$, $C_{14}H_{29}$ and $C_{16}H_{33}$ substituent, respectively, at one of the imidazole nitrogens, as represented by (3) in FIG. 1). For longer chains, such as C12 to C16, the product is isolated as a white precipitate.

(3)-C8: $^1$H NMR (MeOD): δ 9.21 (s, 1H), 7.76 (s, 1H), 7.65 (d, 2H), 7.45 (d, 2H), 7.34 (d, 2H), 7.12 (s, 1H), 6.98 (s, 1H), 5.43 (s, 2H), 5.27 (s, 2H), 4.23 (m, 2H), 1.90 (b, 2H), 1.32 (b, 10H), 0.89 (t, 3H).

(3)-C10: $^1$H NMR (MeOD): δ 9.21 (s, 1H), 7.76 (s, 1H), 7.65 (d, 2H), 7.45 (d, 2H), 7.34 (d, 2H), 7.12 (s, 1H), 6.98 (s, 1H), 5.40 (s, 2H), 5.26 (s, 2H), 4.20 (m, 2H), 1.90 (b, 2H), 1.32 (b, 14H), 0.89 (t, 3H).

(3)-C12: $^1$H NMR (MeOD): δ 9.21 (s, 1H), 7.76 (s, 1H), 7.65 (d, 2H), 7.45 (d, 2H), 7.34 (d, 2H), 7.12 (s, 1H), 6.98 (s, 1H), 5.43 (s, 2H), 5.27 (s, 2H), 4.23 (m, 2H), 1.90 (b, 2H), 1.32 (b, 18H), 0.90 (t, 3H).

(3)-C14: $^1$H NMR (DMSO-D6): δ 9.27 (s, 1H), 7.80 (m, 3H), 7.38 (d, 2H), 7.31 (d, 2H), 7.17 (s, 1H), 6.89 (s, 1H), 5.39 (s, 2H), 5.20 (s, 2H), 4.11 (m, 2H), 1.77 (b, 2H), 1.25 (b, 22H), 0.85 (t, 3H).

(3)-C16: $^1$H NMR (DMSO-D6): δ 9.28 (s, 1H), 7.80 (m, 3H), 7.38 (d, 2H), 7.32 (d, 2H), 7.18 (s, 1H), 6.90 (s, 1H), 5.39 (s, 2H), 5.20 (s, 2H), 4.15 (m, 2H), 1.78 (b, 2H), 1.23 (b, 26H), 0.85 (t, 3H).

(3)-Cy: $^1$H NMR (DMSO-D6): δ 9.28 (s, 1H), 7.80 (m, 3H), 7.38 (d, 2H), 7.31 (d, 2H), 7.17 (s, 1H), 6.90 (s, 1H), 5.40 (s, 2H), 5.20 (s, 2H), 4.03 (m, 2H), 0.91-1.79 (m, 11H).

Synthesis of (4)

1,2-bis(N-imidazole-1-ylmethyl)benzene, (2) (238 mg, 1 mmol) was added to a DMF solution of α,α'-dichloro-p-xylene (5 mmol). The resulting solution was stirred at 90° C. for 8 h. The reaction mixture was cooled down and filtrated to remove insoluble part. The solvent was removed under vacuum. Product 4 was purified by re-precipitation. $^1$H NMR (CD$_3$OD): d 7.35-7.70 (m, 18H), 5.68 (s, 4H), 5.52 (s, 4H), 5.43 (s, 4H).

Synthesis of the Final Compound

For Compound 1, (3)-C6 (364 mg, 1 mmol) was added to a DMF solution of 4 (294, 0.5 mmol). The resulting solution was stirred at 90° C. After overnight stirring, the solution was centrifuged and the solution decanted. The solid precipitates were then washed with DMF and further purified by re-precipitation from MeOH to yield the product as a white solid. $^1$H NMR (MeOD): δ 9.35 (s, 6H), 7.35-7.70 (m, 32H), 5.70 (s, 4H), 5.49 (m, 16H), 4.24 (m, 2H), 1.89 (b, 2H), 1.34 (b, 6H), 0.90 (t, 3H).

The same procedure was used to synthesize the other compounds, namely Compound 2 to Compound 7.

Compound 2: $^1$H NMR (MeOD): δ 7.34-7.70 (m, 32H), 5.67 (s, 4H), 5.47 (m, 16H), 4.22 (m, 2H), 1.91 (b, 2H), 1.32 (b, 10H), 0.90 (t, 3H).

Compound 3: $^1$H NMR (MeOD): δ 9.35 (s, 6H), 7.35-7.70 (m, 32H), 5.70 (s, 4H), 5.50 (m, 16H), 4.24 (m, 2H), 1.91 (b, 2H), 1.35 (b, 14H), 0.90 (t, 3H).

Compound 4: $^1$H NMR (MeOD): δ 9.35 (s, 6H), 7.35-7.70 (m, 32H), 5.70 (s, 4H), 5.47 (m, 16H), 4.23 (m, 2H), 1.90 (b, 2H), 1.32 (b, 18H), 0.90 (t, 3H).

Compound 5: $^1$H NMR (MeOD): δ 9.35 (s, 6H), 7.35-7.70 (m, 32H), 5.70 (s, 4H), 5.47 (m, 16H), 4.23 (m, 2H), 1.89 (b, 2H), 1.33 (b, 22H), 0.90 (t, 3H).

Compound 6: $^1$H NMR (MeOD): δ 7.35-7.70 (m, 32H), 5.70 (s, 4H), 5.46 (m, 16H), 4.23 (m, 2H), 1.90 (b, 2H), 1.32 (b, 26H), 0.90 (t, 3H).

Compound 7: $^1$H NMR (MeOD): δ 9.35 (s, 6H), 7.35-7.70 (m, 32H), 5.70 (s, 4H), 5.49 (m, 16H), 4.09 (m, 2H), 0.98-1.89 (m, 11H).

Example 3

Amphiphilicity of the Representative Compounds

The calculated log $P_{O/W}$ value of the representative compounds of Example 1 varied from −6.06 (Compound 7) to 0.27 (Compound 6) as shown in Table 2.

The MIC values of all 7 oligomer compounds synthesized are presented in Table 2. The MIC values of all these oligomer compounds are in the low ppm range.

Example 5

Hemolysis

Before these materials can be used in systemic applications, selectivity of these materials for microbial cells over mammalian cells should also be considered. Such selectivity is often determined by observation of hemolysis. Hemolysis was performed in the following manner fresh rat red blood cells (RBCs) were diluted with PBS buffer to give an RBC stock suspension (4 vol % blood cells). A 100 μL aliquot of RBC stock was added to a 96-well plate containing 100 mL oligomer compound stock solutions of various concentrations (serial 2-fold dilution in PBS). After 1 h incubation at 37° C., The contents of each well was pipetted into a microcentrifuge tube and then centrifuged at 4000 rpm for 5

TABLE 2

Minimum Inhibitory Concentrations (MIC) and Selectivity Indices of IBN-1 Analogues.[a]

|  | LogP | MIC | | | | | $HC_{10}$ | Selectivity Index |
| --- | --- | --- | --- | --- | --- | --- | --- | --- |
|  |  | S. A. | E. coli | P. A. | C. A. | GM |  |  |
| Compound 1 | −5.91 | 4 | 8 | 8 | 16 | 8 | >100000 | >>1000[b] |
| Compound 2 | −5.56 | 4 | 8 | 16 | 16 | 9.51 | 12500 | 1314 |
| Compound 3 | −5.03 | 4 | 8 | 8 | 31 | 9.44 | 500 | 25 |
| Compound 4 | −3.70 | 4 | 8 | 16 | 31 | 11.22 | 31 | 2.81 |
| Compound 5 | −1.75 | 4 | 16 | 16 | 31 | 13.35 | 15 | 1.15 |
| Compound 6 | 0.27 | 8 | 16 | 16 | 62 | 18.88 | 15 | 0.83 |
| Compound 7 | −6.06 | 8 | 16 | 16 | 31 | 15.87 | 12500 | 787 |
| IBN-1 | −6.14 | 3 | 4 | 31 | 31 | 10.36 | >100000 | >>1000[b] |

[a]MIC values are in ugmL$^{-1}$; Log P is calculated Molinspiration Property Engine (v2013.09); S. A.: *S. aureus*; P. A.: *P. aeruginosa*; C. A.: *C. Albicans*; GM: geometric mean of the MICs of the 4 microbes.
[b]Did not induce ~10% hemolysis at maximum concentration tested (100,000 ppm); Selectivity index = $HC_{10}$/GM.

Example 4

Minimum Inhibitory Concentration

*Staphylococcus aureus* (ATCC 6538, gram-positive), *Escherichia coli* (ATCC 25922, gram-negative), *Pseudomonas aeruginosa* (gram-negative), and *Candida albicans* (ATCC 10231, yeast) were used as representative microorganisms to challenge the antimicrobial functions of the imidazolium salts. All bacteria and yeast were stored frozen at −80° C., and were grown overnight at 37° C. in Tryptic Soy broth (TSB) prior to experiments. Yeast was grown overnight at 22° C. in Yeast Mold (YM) broth. Subsamples of these cultures were grown for 3 h further and diluted to give an optical density value of 0.07 at 600 nm, corresponding to 3×10$^8$ CFU mL$^{-1}$ (MacFarland's Standard).

The oligomer compounds were dissolved in PBS at a concentration of 1 mg mL and the minimal inhibitory concentrations (MICs) were determined by microdilution assay. Typically, a 100 μL microbial solutions (containing 3×10$^8$ cells mL-1) were added to 100 μL of PBS containing the test imidazolium salts (normally ranging from 500 mg mL to 2 mg mL in serial two-fold dilutions) in each well of the 96-well microtiter plate. The plates were incubated at 37° C. for 24 h with shaking at 300 rpm, with monitoring at the 2, 4, 6, 8, and 24 h time points. The minimum inhibitory concentrations were taken as the concentration of the antimicrobial oligomer compound at which no microbial growth was observed with the microplate reader. Broth and PBS solution containing microbial cells alone were used as negative controls, and experiments were run in triplicates.

min. Hemolytic activity was determined as a function of hemoglobin release by measuring OD576 of 100 mL of the supernatant. A control solution that contained only PBS was used as a reference for 0% hemolysis. 100% hemolysis was measured by adding 0.5% Triton-X to the RBCs.

$$\% \text{ Hemolysis} = \frac{OD576 \text{ (oligomer)} - OD576 \text{ (PBS)}}{OD576 \text{ (Triton-X)} - OD576 \text{ (PBS)}} \times 100 \quad \text{[MATH. 1]}$$

It was noted that hemolysis of red blood cells was not induced at the respective MIC values, for all the oligomer compounds synthesized, as shown in FIG. 2.

Example 6

Selectivity Assessment

The selectivity of the materials was also further assessed, by calculating the selectivity indices (SI), a measure and a comparison of safety and efficacies of each oligomer compound. The selectivity index of each oligomer compound was calculated as the ratio of $HC_{10}$ value (defined as the lowest oligomer compound concentration that induces 10% or more hemolysis) to the GM (geometric mean of the MICs of the 4 microbes tested). Herein, the more stringent control of $HC_{10}$ value was chosen over the $HC_{50}$ value often reported in literature. A selectivity index of more than 10 would indicate the potential utility of the material in both systemic and external applications.

As seen in Table 2, only the shorter chain analogues of Compound 1, Compound 2, Compound 3 and Compound 7 met this requirement of high selectivity. As shown in FIG. 3, the MIC values increased as the alkyl chain length increased. At the same time, the hemolytic ability of these materials also increased with the alkyl chain length. These observations correlate well with the calculated polarities. The exception of Compound 7 also indicates that the properties of these imidazolium oligomer compounds are highly dependent on the structure of terminal groups. It has been well reported that biomolecules of higher hydrophobicity are generally more potent as a drug, but are concurrently more toxic. However, for our current imidazolium oligomer compounds, the molecules with longer hydrophobic tails exhibit less potency against various microbes. From FIG. 3, the compounds found within the rectangular box, Compound 1 and Compound 2, are the optimal candidates with the highest potency, while resulting in minimal hemolysis.

Example 7

Minimum Biocidal Concentration

While MIC values provide a perspective of the efficacy of a compound as an antimicrobial, it does not distinguish the compound's ability to either inhibit the growth of microbes, or eliminate the microbes completely. A compound is only considered bactericidal if the minimum biocidal concentration (MBC) is less than 4 times the MIC value.

To determine the minimum bacteriocidal concentration, the microbes were inoculated and prepared according to the procedure for MIC determination. The microbes were then treated with the oligomer compound at various concentrations of 0.5 MIC, MIC, 2 MIC, and were incubated at 37° C. for 24 hours at constant shaking of 300 rpm. The bacterial samples were taken out of each well after the aforementioned period, and subjected to a series of 10-fold dilutions. 20 uL of the diluted sample was then streaked across an agar plate, before incubation of the plate at 37° C. for 24 h. Colony forming units (CFU) were counted after overnight incubation, and the results were calculated according to the formula:

$$\text{Log reduction} = \log_{10}(\text{number of colonies } (PBS \text{ control})X \text{ dilution factor}) - \log_{10}(\text{number of colonies (oligomer)}X \text{ dilution factor})$$

$$\% \text{ kill} = \frac{(\text{Oligomer } X \text{ dilution factor})}{(\text{Control } X \text{ dilution factor})} \times 100$$

[MATH. 2]

Compound 1 and Compound 2 were further selected for the MBC test. As shown in Table 3, Compound 1 and Compound 2 exhibited clear bactericidal behavior, in which more than 99.999% killing of microbes were attained when treated with the respective MIC concentrations for 24 hours. More surprisingly, almost effective killing was also observed even with half the MIC concentration.

TABLE 3

Killing efficiency (24 h) of Compound 1 and Compound 2 at different concentrations.

| | | Compound 1 | | Compound 2 | |
|---|---|---|---|---|---|
| | Concentration | Log reduction | % killing | Log reduction | % killing |
| S. aureus | 0.5 MIC | 3.69 ± 0.335 | 99.975 | 1.71 ± 0.032 | 98.03 |
| | MIC | 5.35 ± 0.094 | 99.999 | 11.82 ± 0.067 | >99.999 |
| | 2 MIC | 7.28 ± 0.036 | >99.999 | 13.38 ± 0.337 | >99.999 |
| E. coli | 0.5 MIC | 1.48 ± 0.212 | 97.692 | 2.67 ± 0.128 | 99.779 |
| | MIC | 7.53 ± 0.173 | >99.999 | 7.11 ± 0.123 | >99.999 |
| | 2 MIC | 8.40 ± 0.403 | >99.999 | 7.19 ± 0.149 | >99.999 |

Example 8

Time Kill Kinetics

Time kill studies of the soligome compounds against *E. coli* were also studied. The experimental setup for time kill kinetics was similar to the set up for MBC determination. The microbes were treated with oligomer compounds at 4MIC concentration, and samples were taken out of each well at 2 minutes. 500 µl of cell suspension was removed, rescued by a series of 10-fold dilutions with growth medium, and kept on ice until plating. For plating, 50 µl to 200 µl of the diluted samples was spread on growth medium agar plates and colonies were counted after overnight incubation at 37° C.

It was surprising that Compound 1 and Compound 2 were able to efficiently kill the microbes ($3 \times 10^8$ cells $mL^{-1}$) instantly, as shown in Table 4. More than 99.9% of killing was observed within two minutes at 32 ppm concentration of oligomer compounds, as compared to 83% killing for the IBN-1 oligomer.

To further investigate the phenomena, experiments of positive controls with Compound 4 and 1-Methyl-3-octyl imidazolium bromide (monomeric imidazolium with Compound 2 alkyl chain) were performed. MIC studies on 1-Methyl-3-octyl imidazolium bromide revealed a MIC value of 1000 ppm, more than 100 times of Compound 2. It was observed that the Compound 3, Compound 4 analogue also effected instantaneous elimination. Most of previously reported fast killing antimicrobials, such as AMPs and modified silver nano-particles, exhibited microbe killing in a time scale of minutes to hours. Such fast killing kinetic with simple oligomer compounds or polymers has yet to be reported. From these observations, it can be deduced that the hydrophobic aliphatic chains do contribute to the advantageous instantaneous killing, in which the facial combination of hydrophobic end groups and the multiple charged imidazolium oligomer chain is the key structure-activity implication for this ultra-efficient fast killing behavior. In contrast, monomeric imidazolium salts with simple alkyl chains are ineffective and lack antimicrobial activities.

TABLE 4

Imidazolium oligomer compounds treat *E. coli* at 4 MIC in two minutes.

| | IBN-1 | Compound 1 | Compound 2 | Compound 3 | Compound 4 |
|---|---|---|---|---|---|
| Log reduction | 0.79 ± 0.11 | 2.85 ± 0.51 | 3.11 ± 0.14 | 3.49 ± 0.18 | 3.69 ± 0.11 |
| % kill | 83.33 | 99.8 | >99.9 | >99.9 | >99.9 |

Example 9

Critical Micellar Concentration

The introduction of long n-alkyl chains render the molecules amphiphilic, and this may trigger the self-assembly processes of the molecules. Enhanced microbial action may be possible with prior microstructure formation of the polymer into micelles before treatment of the microbes. Most amphiphilic molecules are able to form micelles in aqueous solutions, and for some antimicrobial compounds, such self-assembly may be critical to their efficacy. The synthesized compounds, having structures consisting of hydrophobic tails attached on both ends of a hydrophilic block, were studied for their ability to form micellar microstructures.

The CMC values of the oligomer compounds were determined in both deionised (DI) water and PBS, using a LS50B luminescence spectrometer (Perkin Elmer, United States) and employing pyrene as a fluorescent probe. A known weight of the oligomer compound was dissolved in either 2 mL of DI water or PBS in a 4 mL glass vial and serial dilutions were effected. 10 μL of pyrene stock solution in acetone ($6.16\times10^{-5}$ M) was added to each vial containing 1 mL of a known concentration of the oligomer compound, and the acetone was then evaporated at room temperature. The solution was allowed to equilibrate overnight and the final concentration of pyrene in each vial was $6.16\times10^{-7}$ M. The excitation spectra of the solutions were scanned from 300 to 360 nm with an emission wavelength of 395 nm, and both the excitation and emission bandwidths were set at 2.5 nm. The intensity ratios ($I_{337}/I_{334}$) were plotted against polymer concentration. The CMC value was given by the intersection of the tangent to the curve at the inflection and the tangent of the points at low polymer concentrations.

It was observed that the only oligomer compound with the long hydrophobic n-alkyl chains of Compound 4 to Compound 6 were able to form micelles. Such oligomer compounds form micelles at concentrations lower than that of the MIC values in PBS solution, where Compound 4, Compound 5 and Compound 6 were able to form micelles at 10.9, 4.9 and 1.3 ppm respectively, as shown in Table 5. In comparison, a sharp point of inflection indicating the critical micellar concentrations was not observed for the shorter chain analogues, Compound 1, Compound 2, Compound 3, and the IBN-1 oligomer (FIG. 4). This could mean that these oligomer compounds exist freely in solution, with fleeting aggregations due to non-specific interactions. More significantly, it revealed that micellar microstructure formation of the oligomer compounds was not essential to antimicrobial action. In fact, the longer chain oligomers often had higher MIC values than that of the shorter chains and the original IBN-1.

TABLE 5

CMC Values of representative compounds in DI $H_2O$ and PBS buffer solution

|  | CMC in DI $H_2O$ (ppm) | CMC in PBS (ppm) |
|---|---|---|
| Compound 4 | 938.5 | 10.9 |
| Compound 5 | 200.3 | 4.9 |
| Compound 6 | 38.5 | 1.3 |

Example 10

Gelling Properties of Imidazolium Compounds

Gels were prepared by weighing the imidazolium oligomer compounds directly into 4 mL glass vials and subsequently adding a known weight or volume of the solvent. The vials containing both the imidazolium and the solvent were either vortexed or sonicated to ensure that the imidazolium was dissolved and dispersed thoroughly before being placed in a 4° C. fridge overnight. The tube inversion test method was used to examine gel formation in different solvents.

TABLE 6

Concentration of oligomer compounds to form gels in various solvents

| Solvent | Compound 1 | Compound 2 | Compound 3 | Compound 4 | Compound 5 | Compound 6 |
|---|---|---|---|---|---|---|
| Ethylene glycol | Solution | Solution | Solution | Solution | Solution | Gel (4.7 wt %) |
| Glycerol | Solution | Solution | Solution | Solution | Solution | Gel (6.3 wt %) |
| Acetonitrile | Insoluble | Insoluble | Insoluble | Insoluble | Insoluble | Insoluble |
| Acetone | Insoluble | Insoluble | Insoluble | Insoluble | Insoluble | Insoluble |
| nBuOH | Gel (9.2 wt %) | Gel (11.3 wt %) | Gel (7.9 wt %) | Gel (5.8 wt %) | Gel (5.3 wt %) | Gel (6.9 wt %) |
| nPrOH | Gel (7.8 wt %) | Gel (9.8 wt %) | Gel (7.9 wt %) | Gel (7.2 wt %) | Gel (5.3 wt %) | Gel (6.9 wt %) |
| EtOH | Gel (11 wt %) | Gel (11 wt %) | Gel (12 wt %) | Gel (9.0 wt %) | Gel (12.9 wt %) | Gel (9.6 wt %) |

During the study of the self-assembly properties of the amphiphilic chains, it was found that Compound 6 was able to form opaque gels in the solvents that are frequently used in general disinfection applications, such as glycerol and ethylene glycol. While Compound 4 did not form a gel in binary mixtures of water/ethanol and glycerol/ethanol, the oligomers were able to form gels in pure ethanol at a concentration of less than 10 wt %. We expanded the gelling ability studies to all the oligomers in the series and various alcohols, and were delighted that all the oligomers were able to form opaque gels in ethanol, n-propanol and n-butanol, as shown in Table 6. It must be noted that both IBN-1 and Compound 7 were not able to form gels in any of the solvents, and no gels were formed with the use of branched alcohols of isopropanol and tert-butanol.

While gels were stable at ambient temperatures, it was observed that the gels were thixotropic; in which when the vials containing the gels were vortexed, it becomes fluid but consequently sets into a solid-like state in the course of a few minutes. This suggested that the gels were weak gels.

Example 11

Rheology

Rheology experiments were performed at room temperature using a control strain rheometer (ARES G2, U.S.A). The dynamic storage modulus (G') was examined as a function of frequency from 0.1 to 100 rad/s. The measurements were carried out at strain amplitude of 5% to ensure the linearity of viscoelasticity. In addition, viscosity of the gel was also examined as a function of shear rate from 0.1 to 50/s.

Rheology characterization revealed that the gels are indeed weak gels, with low G' values (FIG. 5), and the viscosity of the gels decreased with increasing shear rate (FIG. 6), indicating thixotropic behaviour. This property would be ideal for applications as antimicrobial handrubs, or surface treatments, as the gels can then be easily spread over a finite surface area.

Example 12

SEM Observation

SEM imaging was done on the Compound 2 xerogels (FIG. 7B). The morphologies of the organogel microstructure were observed using a field emission SEM (JEOL JSM-7400F) operated at an accelerating voltage of 10 keV. The gels were dried via supercritical drying, and stored in under anhydrous conditions, either in a glovebox or a dessicator prior to imaging.

It was observed that these gels had a spongy nature to them, as shown in FIG. 7A. FIG. 7A shows vials containing Compound 4, Compound 5 and Compound 6 which form gels rather than solutions in n-butanol. This suggests that these are likely to be fluid matrix organogels, in which the only forces holding them together are simple chain entanglements. These amphiphilic structures are postulated to form loose aggregations at low concentrations, and at higher concentrations, form fibrillar networks that are intertwined in the solvent mix, trapping the solvent in the matrix.

Example 13

Self-Gelation

It is well known that many amphiphilic structures, such as block-co-polymers and peptides, could form gels via self-assembly to certain microstructures. While most of antimicrobial materials can assume amphiphilic structures, self-gelation is often not realized. There have been reports of antimicrobial materials that can assemble to hydrogels including peptides and block polymers based on chitin and lactic acid materials. However, these assembly processes are typically triggered by co-gelation polymers or grafting antimicrobial material with other polymers. Here, the unique sandwich-type amphiphilic structure of Compound 1 to Compound 6 imidazolium oligomer compounds provides novel properties including highly active antimicrobial activities and the added ability to self-assemble to organogels, the mechanism for which is proposed in FIG. 7C. These properties are especially attractive for applications in personal hygiene, sterilization and other health care areas.

Comparative Example 1

For the previously reported imidazolium oligomer IBN-1, its amphiphilicity was dominated by its polar segments. The calculated log $P_{o/w}$ is −6.14 and total polar surface area (TPSA) is 52.91.

INDUSTRIAL APPLICABILITY

The compound, pharmaceutical composition and gel disclosed in the present application may be suitable for applications in personal hygiene, sterilization and other health care areas. The compound, pharmaceutical composition and gel may be useful in sterilization applications, including antimicrobial handrubs and surface treatments.

In particular, the compound, pharmaceutical composition and gel may have applications in medical devices, hospital surfaces, textiles, food packaging, children's toys, electrical appliances, handwashing applications, as well as dental equipment.

It will be apparent that various other modifications and adaptations of the invention will be apparent to the person skilled in the art after reading the foregoing disclosure without departing from the spirit and scope of the invention and it is intended that all such modifications and adaptations come within the scope of the appended claims.

What is claimed is:

1. A compound having the following Formula (I):

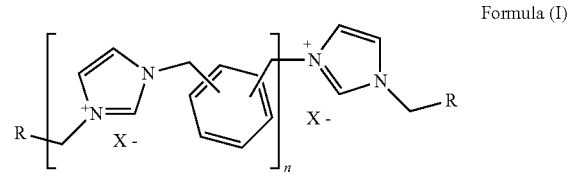

Formula (I)

wherein R is an optionally substituted aliphatic group that is linear, cyclic, saturated, unsaturated or any combination thereof; n is an integer of 5 to 10; and X is an anionic counterion.

2. The compound according to claim 1, wherein R is an optionally substituted linear alkyl, optionally substituted branched alkyl, optionally substituted cyclic alkyl, optionally substituted alkyl halide, optionally substituted alkyl alkene, optionally substituted alkyl alkyne or any combination thereof.

3. The compound according to claim 2, wherein R may be selected from the group consisting of saturated liner alkyl or saturated cyclic alkyl comprising 5 to 20 carbon atoms.

4. The compound according to claim 3, wherein R is selected from the group consisting of cyclohexylmethyl ($C_6H_{11}CH_2$), hexyl ($C_6H_{13}$), octyl ($C_8H_{17}$), decyl ($C_{10}H_{21}$), dodecyl ($C_{12}H_{25}$), tetradecyl ($C_{14}H_{29}$), hexadecyl ($C_{16}H_{33}$) and any mixture thereof.

5. The compound according to claim 1, wherein n is 5, 6 or 7.

6. The compound according to claim 1, wherein X is halogen, carbonate, phosphate, nitrate, sulfate, carboxylate or any combination thereof.

7. The compound according to claim 1, wherein the benzene ring in Formula (I) is substituted at the meta-position, ortho-position, para-position or any combination thereof.

8. The compound according to claim 1, wherein the compound has the following Formula (II):

Formula (II)

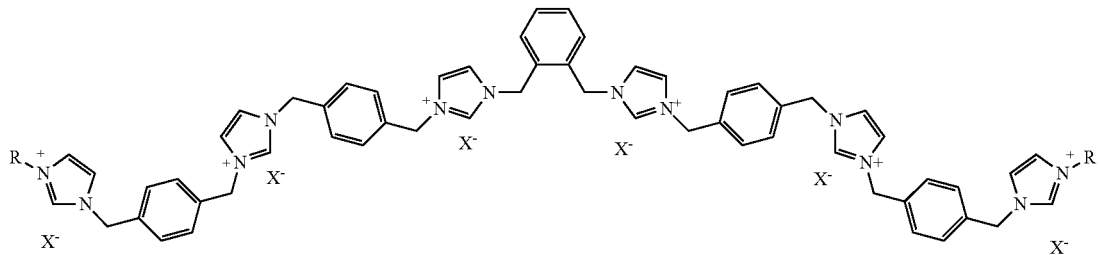

wherein R is selected from the group consisting of cyclohexylmethyl ($C_6H_{11}CH_2$), hexyl ($C_6H_{13}$), octyl ($C_8H_{17}$), decyl ($C_{10}H_{21}$), dodecyl ($C_{12}H_{25}$), tetradecyl ($C_{14}H_{29}$), hexadecyl ($C_{16}14_{33}$) and any mixture thereof.

9. The compound according to claim 1, wherein the compound is amphiphilic.

10. The compound according to claim 3, wherein R may be selected from the group consisting of saturated liner alkyl or saturated cyclic alkyl further comprising 6 to 16 carbon atoms.

* * * * *